US010308980B2

(12) United States Patent
Lothe et al.

(10) Patent No.: US 10,308,980 B2
(45) Date of Patent: Jun. 4, 2019

(54) METHODS AND BIOMARKERS FOR ANALYSIS OF COLORECTAL CANCER

(71) Applicants: Ragnhild A. Lothe, Oslo (NO); Trude Holmeide Agesen, Oslo (NO); Anita Sveen, Oslo (NO); Guro Elisabeth Lind, Oslo (NO); Arild Nesbakken, Royken (NO); Rolf Inge Skotheim, Oslo (NO)

(72) Inventors: Ragnhild A. Lothe, Oslo (NO); Trude Holmeide Agesen, Oslo (NO); Anita Sveen, Oslo (NO); Guro Elisabeth Lind, Oslo (NO); Arild Nesbakken, Royken (NO); Rolf Inge Skotheim, Oslo (NO)

(73) Assignee: OSLO UNIVERSITETSSYKEHUS HF, Oslo (NO)

( * ) Notice: Subject to any disclaimer, the term of this patent is extended or adjusted under 35 U.S.C. 154(b) by 382 days.

(21) Appl. No.: 14/354,310

(22) PCT Filed: Nov. 5, 2012

(86) PCT No.: PCT/IB2012/002844
§ 371 (c)(1),
(2) Date: Apr. 25, 2014

(87) PCT Pub. No.: WO2013/064908
PCT Pub. Date: May 10, 2013

(65) Prior Publication Data
US 2014/0302100 A1 Oct. 9, 2014

Related U.S. Application Data

(60) Provisional application No. 61/555,762, filed on Nov. 4, 2011.

(51) Int. Cl.
*C12Q 1/6813* (2018.01)
*C12Q 1/6886* (2018.01)
(52) U.S. Cl.
CPC ......... *C12Q 1/6813* (2013.01); *C12Q 1/6886* (2013.01); *C12Q 2563/159* (2013.01); *C12Q 2600/118* (2013.01); *C12Q 2600/158* (2013.01)
(58) Field of Classification Search
None
See application file for complete search history.

(56) References Cited

U.S. PATENT DOCUMENTS

2005/0287544 A1 12/2005 Bertucci et al.
2008/0058432 A1* 3/2008 Wang .................. C12Q 1/6886
514/789
2011/0097423 A1 4/2011 Beauchamp et al.

FOREIGN PATENT DOCUMENTS

WO 2004/001072 12/2004
WO 2007/082099 7/2007
WO 2009/045115 4/2009
WO 2010/047448 4/2010
WO 2011/094483 8/2011

OTHER PUBLICATIONS

Lin (Clin Cancer Res 2007;13(2) pp. 498-507).*
Ogawa (Clin Cancer Res 2005:11(8) Apr. 15, 2005).*
Wong (BioTechniques 39:75-85 (Jul. 2005)).*
Wang (Oncogene 2005 vol. 24 pp. 5637-5647).*
Katkoori (Cancer Res 2010 vol. 70 (8 Suppl) Abstract nr4655).*
Cardoso (Biochimica et Biophysica Acta 1775 (2007) pp. 103-137).*
Ochiumi (International Journal of Oncology vol. 29 pp. 105-116 2006).*
Agesen T. et al., "ColoGuideEx: a robust gene classifier specific for stage II colorectal cancer prognosis," Gut, 2012, vol. 61, No. 11, pp. 1560-1567.
Bacon AL. et al., "Selective silencing of the hypoxia-inducible factor 1 target gene BNIP3 by histone deacetylation and methylation in colorectal cancer." Oncogene, 2007;26(1):132-41.
Barrier A. et al., "Colon cancer prognosis prediction by gene expression profiling." Oncogene, 2005;24(40):6155-64.
Barrier A. et al., "Prognosis of stage II colon cancer by non-neoplastic mucosa gene expression profiling." Oncogene. 2007;26(18):2642-8.
Cui T. et al., "DSC3 expression is regulated by p53, and methylation of DSC3 DNA is a prognostic marker in human colorectal cancer." Br J Cancer. 2011;104(6):1013-9.
Greenbaum D. et al., "Comparing protein abundance and MRNA expression levels on a genomic scale," Genome Biology, 2003, vol. 40, No. 9, pp. 117.01-117.08.
Greenbaum D. et al., "Interrelating different types of genomic data, frm proteome to secretome: Oming in on function," Genome Research, 2001, vol. 11, No. 9, pp. 1463-1468.
Grone J. et al, "Molecular profiles and clinical outcome of stage UICC II colon cancer patients." Int J Colorectal Dis. 2011;26(7):847-58.
Herath N. et al., "Complex expression patterns of Eph receptor tyrosine kinases and their ephrin ligands in colorectal carcinogenesis." Eur J Cancer, 2012;48(5):753-62.
International Search Report and Written Opinion, International Patent Application No. PCT/IB2012/002844, dated Apr. 19, 2013.
Japanese Office Action, corresponding JP Patent Application No. 2014-539425, dated Jul. 14, 2015, English translation provided.
Jeffery N. et al., "The matrix metalloproteinase/tissue inhibitor of matrix metalloproteinase profile in colorectal polyp cancers." Histopathology. 2009; 54(7):820-8.
Jiang Y. et al., "Development of a clinically feasible molecular assay to predict recurrence of stage II colon cancer." J Mol Diagn. 2008;10(4):346-54.

(Continued)

Primary Examiner — Amanda Haney
(74) Attorney, Agent, or Firm — Casimir Jones S.C.; J. Mitchell Jones

(57) ABSTRACT

The present invention relates to methods and biomarkers (e.g., gene expression biomarkers) for detection of colorectal cancer in biological samples (e.g., tissue samples, biopsy samples, stool samples, blood samples, plasma samples, serum samples). In some embodiments, methods and biomarkers of the present invention find use in detection of colon cancer and in providing a prognosis to colorectal cancer patients.

10 Claims, 6 Drawing Sheets

(56) References Cited

OTHER PUBLICATIONS

Jiang Z. et al., "CXCL10 expression and prognostic significance in stage II and III colorectal cancer." Mol Biol Rep. 2010;37(6):3029-36.

Kasamatsu A. et al., "Identification of candidate genes associated with salivary adenoid cystic carcinomas using combined comparative genomic hybridization and oligonucleotide microarray analyses," International Journal of Biochemistry and Cell Biology, 2005, vol. 37, No. 9, pp. 1869-1880.

Kelley et al., "Prognostic and predictive markers in stage II colon cancer: is there a role for gene expression profiling?" Clin Colorectal Cancer. 2011;10(2):73-80.

Kurokawa K. et al., "Brief naturalistic stress induces an alternative splice variant of SMG-1 lacking exon 63 in peripheral leukocytes," Neuroscience Letters, 2010, pp. 128-132.

Nguyen Q. et al., "Inhibition of vascular endothelial growth factor (VEGF)-165 and semaphorin 3A-mediated cellular invasion and tumor growth by the VEGF signaling inhibitor ZD4190 in human colon cancer cells and xenografts." Mol Cancer Ther. 2006;5(8):2070-7.

Oerntoft T.F. et al., "Genome-wide study of gene copy numbers, transcripts, and protein levels in pairs of non-invasive and invasive human transitional cell carcinomas," Molecular & Cellular Proteomics, 2002, vol. 1, No. 1, pp. 37-45.

Ogawa K. et al., "Clinical significance of human kallikrein gene 6 messenger RNA expression in colorectal cancer." Clin Cancer Res. 2005;11(8)2889-93.

Salazar R. et al., "Gene expression signature to improve prognosis prediction of stage II and III colorectal cancer." J Clin Oncol. 2011;29(1)17-24.

Schepeler T. et al., "Diagnostic and prognostic microRNAs in stage II colon cancer." Cancer Res. 2008;68 (15):6416-24.

Smith JJ et al., "Experimentally derived metastasis gene expression profile predicts recurrence and death in patients with colon cancer." Gastroenterology. 2010;138(3):958-68. Epub Nov. 13, 2009.

Sveen A. et al., "Transcriptome instability in colorectal cancer identified by exon microarray analyses: Associations with splicing factor expression levels and patient survival.," Genome Medicine, 2011, 3:32.

Traicoff J. et al., "Characterization of the human polymeric immunoglobulin receptor (PIGR) 3'UTR and differential expression of PIGR mRNA during colon tumorigenesis." J Biomed Sci. 2003;10(6 Pt 2)792-804.

Webber E. et al., "Oncotype DX tumor gene expression profiling in stage II colon cancer. Application: prognostic, risk prediction." PLoS Curr. 2010;2; pii: RRN1177.

Yano Y. et al., "Expression and localization of ecto-nucleotide pyrophosphatase/phosphodiesterase I-3 (E-NPP3/CD203c/PD-I beta/B10/gp130RB13-6) in human colon carcinoma." Int J Mol Med. Nov. 2003;12(5):763-6.

* cited by examiner a b c

A) Distribution of univariate p-values

B) Distribution of gene expression variance

● Filtered gene set (n = 3339)   ● 13-gene prognostic classifier

C) Gene expression correlation

A

B

METHODS AND BIOMARKERS FOR ANALYSIS OF COLORECTAL CANCER

CROSS-REFERENCE TO RELATED APPLICATIONS

This application is a 371 U.S. National Phase Entry of pending International Patent Application No. PCT/IB2012/002844, International Filing Date Nov. 5, 2012, which claims priority to expired U.S. Provisional Patent Application No. 61/555,762, filed Nov. 4, 2011, the contents of which are incorporated by reference in their entireties.

FIELD OF THE INVENTION

The present invention relates to methods and biomarkers (e.g., gene expression biomarkers) for detection of colorectal cancer in biological samples (e.g., tissue samples, biopsy samples, stool samples, blood samples, plasma samples, serum samples). In some embodiments, methods and biomarkers of the present invention find use in detection of colon cancer, providing a prognosis to colorectal cancer patients, and in companion diagnostics.

BACKGROUND OF THE INVENTION

Colorectal cancer (CRC) is one of the most common cancer types in both men and women worldwide, with about 1.2 million new cases recorded annually. [1] The prognosis is highly dependent on the tumour stage at time of diagnosis. According to the American Joint Committee on Cancer (AJCC), the 5-year overall survival rate is 93%, 83%, 60% and 8% in stage I, II, III, and IV, respectively. [2] However, the prognosis for stage IIb patients (pT3-4, lymph node negative) is significantly lower (72%) than for those with stage IIIa (pT1-2, lymph node positive; 83%). [2]

Adjuvant chemotherapy significantly improves survival in among stage III CRC and is accepted as standard treatment of these patients. [3] The majority of stage II CRC patients are cured by surgery alone, but perforation of the tumour and few examined lymph nodes are associated with reduced survival, and are usually considered for adjuvant chemotherapy. A proportion of stage II patients without increased risk of relapse based on current clinical factors still develop relapse. One could consider treating all stage II CRC patients with adjuvant chemotherapy, but the effect of this has not been conclusive. [4-6]

This highlights the need for new biomarkers for more precise prediction of high-risk stage II patients, and consequently also improved individualized cancer care.

SUMMARY OF THE INVENTION

The present invention relates to methods and biomarkers (e.g., gene expression biomarkers) for detection of colorectal cancer in biological samples (e.g., tissue samples, biopsy samples, stool samples, blood samples, plasma samples, serum samples). In some embodiments, methods and biomarkers of the present invention find use in detection of colon cancer and in providing a prognosis to colorectal cancer patients.

For example, embodiments of the present invention provide method for diagnosing colon cancer or predicting a prognosis (e.g., of stage I, II or III colorectal cancer) in a subject, comprising: a) contacting a biological sample from a subject (e.g., diagnosed with stage I, II or III colorectal cancer) with a reagent for detecting the level of expression of one or more (e.g., two or more, three or more, 5 or more, ten or more or all 13) genes selected from, for example, PIGR, CXCL13, MMP3, TUBA1B, SESN1, AZGP1, KLK6, EPHA7, SEMA3A, DSC3, CXCL10, ENPP3, or BNIP3; and b) detecting the level of expression of the one or more genes using an in vitro assay, wherein an altered level of expression of the one or more genes provides an indication of a diagnosis of colon cancer or a poor prognosis of the subject. In some embodiments, the biological sample is a tissue sample, a biopsy sample, a blood sample or a stool sample. In some embodiments, a decreased level of expression of one or more of PIGR, CXCL13, MMP3, TUBA1B, and CXCL10 relative to the level of expression in a control sample and/or an increased level of expression of one or more of SESN1, AZGP1, KLK6, EPHA7, SEMA3A, DSC3, ENPP3, and BNIP3 relative to the level of expression in a control sample of the genes is associated with a poor prognosis of the subject. In some embodiments, expression is detected at the nucleic acid level (e.g., mRNA), while in other embodiments it is detected at the protein level. In some embodiments, the prognosis is 5 year recurrence free survival, decreased survival or recurrence or metastasis of the colorectal cancer. In some embodiments, the control sample is a sample from a subject diagnosed with stage I or IV colorectal cancer or a subject not diagnosed with colorectal cancer. In some embodiments, a treatment course of action (e.g., administration of chemotherapy to subjects identified as having a poor prognosis) is determined based on the prognosis.

Further embodiments, provide a kit, comprising: reagents for detecting altered expression in a sample from a subject (e.g., diagnosed with stage I, II or III colorectal cancer) of one or more (e.g., two or more, three or more, 5 or more, ten or more or all 13) genes selected from, for example, PIGR, CXCL13, MMP3, TUBA1B, SESN1, AZGP1, KLK6, EPHA7, SEMA3A, DSC3, CXCL10, ENPP3, or BNIP3. Additional embodiments provide for the use of the kit for diagnosing colorectal cancer or determining a prognosis of a subject diagnosed with colorectal cancer.

In some embodiments, the present invention provides methods for determining a prognosis of colorectal cancer in a subject, diagnosing a colorectal cancer in a subject, predicting a predisposition to colorectal cancer in a subject, predicting the likelihood of recurrence of colorectal cancer in a subject, or selecting a subject with a disease for treatment with a particular therapy, comprising: a) contacting a biological sample from a subject with a colorectal cancer informative reagent for detecting the level of expression of one or more genes selected from the group consisting of PIGR, CXCL13, MMP3, TUBA1B, SESN1, AZGP1, KLK6, EPHA7, SEMA3A, DSC3, CXCL10, ENPP3, BNIP3, PLA2G2A, GZMK, MMP1, AKD1, XRCC4 RAET1L, TTC30A, HAS2, CPE, CXCL9, GBP4, RPS6KA6, ENPP5, RAP1B, DYNLL1, and RPS27L; and b) detecting the level of expression of the one or more genes using the colorectal cancer informative reagent in an in vitro assay, wherein an altered level of expression of the one or more genes provides: an indication of a poor prognosis of the subject, a diagnosis of a colorectal cancer in the subject, a prediction of a predisposition to colorectal cancer in the subject, a prediction of the likelihood of recurrence of colorectal cancer in the subject, or an indication that the subject is a candidate for treatment with a particular therapy. In some embodiments, the colorectal cancer is stage I, II or III.

In some embodiments, the one or more genes comprises a set of two or more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CRE), one of (CXCL10, CXCL9 or GBP4), one of (ENPP3 or RPS6KA6), and one of (BNIP3 or ENPP5). In some embodiments, one or more genes comprises a set of three or more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the one or more genes comprises a set of five or more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the one or more genes comprises a set of ten or more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the one or more genes comprises a set of twelve of more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CRE), one of (CXCL10, CXCL9 or GBP4), one of (ENPP3 or RPS6KA6), and one of (BNIP3 or ENPP5). In some embodiments, one or more genes comprises a set of thirteen genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the one or more genes comprises the set of PIGR, CXCL13, MMP3, TUBA1B, SESN1, AZGP1, KLK6, EPHA7, SEMA3A, DSC3, CXCL10, ENPP3, and BNIP3.

In some embodiments, the biological sample is selected from the group consisting of a tissue sample, a biopsy sample, a blood sample and a stool sample. In some embodiments, the subject has been previously diagnosed with colorectal cancer.

In some embodiments, a decreased level of expression of one or more genes selected from the group consisting of one of (PIGR or PLA2G2A), one of (CXCL13 or GZMK), one of (MMP3 or MMP1), one of (TUBA1B, RAP1B, DYNLL1, or RPS27L), and one of (CXCL10, CXCL9 or GBP4) and combinations thereof relative to a reference level of expression of the genes is associated with a poor prognosis of the subject. In some embodiments, an increased level of expression of one or more genes selected from the group consisting of one of (SESN1 or AKD1), one of (AZGP1 or XRCC4), one of (KLK6 or RAET1L), one of (EPHA7 or TTC30A), one of (SEMA3A or HAS2), one of (DSC3 or CRE), one of (ENPP3 or RPS6KA6), and one of (BNIP3 or ENPP5) relative a reference level of expression of the genes is associated with a poor prognosis of the subject. In some embodiments, the poor prognosis comprises decreased survival. In some embodiments, the poor prognosis comprises recurrence or metastasis of the colorectal cancer. In some embodiments, the reference level is a level from a subject diagnosed with stage I or IV colorectal cancer. In some embodiments, the reference level is a level from a subject not diagnosed with colorectal cancer. In some embodiments, the prognosis comprises 5 year relapse free survival.

In some embodiments, the methods further comprise the step of determining a treatment course of action. In some embodiments, the treatment course of action comprises administering chemotherapy to subjects identified as having a poor prognosis and not administering chemotherapy to subjects identified as having a good prognosis. In some embodiments, the chemotherapy is adjuvant chemotherapy.

In some embodiments, the colorectal cancer informative reagent is selected from the group consisting of a nucleic acid probe or probes that hybridizes to a respective gene product of the one or more genes, nucleic acid primers for the amplification and detection of a respective gene product of the one or more genes, and an antigen binding protein specific for a respective gene product of the one or more genes. In some embodiments, the gene product is an RNA transcript from the gene and the colorectal informative reagent is a nucleic acid probe or probes that hybridizes to the respective gene product of the one or more genes or nucleic acid primers for the amplification and detection of the respective gene product of the one or more genes.

In some embodiments, the present invention provides methods for providing a prognosis related to colorectal cancer in a subject, comprising: a) contacting a biological sample from a subject with a colorectal cancer informative reagent for detecting the level of expression of one or more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5); and b) detecting the level of expression of the one or more genes using the colorectal cancer informative reagent in an in vitro assay, wherein an altered level of expression of the one or more genes is indicative of a poor prognosis related to colorectal cancer in the subject.

In some embodiments, the present invention provides a kit, comprising: one or more colorectal informative reagents for detecting altered gene expression in a sample from a subject having or suspected of having colorectal cancer of one or more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the one or more genes comprises a set of two or more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the one or more genes comprises a set of three or more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the one or more genes comprises a set of five or more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the one or more genes comprises a set of ten or more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the one or more genes comprises a set of twelve of more genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the one or more genes comprises a set of thirteen genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the one or more genes comprises the set of PIGR, CXCL13, MMP3, TUBA1B, SESN1, AZGP1, KLK6, EPHA7, SEMA3A, DSC3, CXCL10, ENPP3, and BNIP3.

In some embodiments, the one or more colorectal informative reagents is a probe(s) that specifically hybridizes to a respective gene product(s) of the one or more genes. In some embodiments, the one or more colorectal informative reagents is a set(s) of primers that amplify a respective gene product(s) of the one or more genes. In some embodiments, the one or more colorectal informative reagents is an antigen binding protein(s) that binds to a respective gene product(s) of the one or more genes. In some embodiments, the one or more colorectal informative reagents is a sequencing primer(s) that hybridizes to and allows sequencing of a respective gene product(s) of the one or more genes.

In some embodiments, the kit is used for determining a prognosis of a subject diagnosed with colorectal cancer. In some embodiments, the kit is used for diagnosing colorectal cancer in a subject. In some embodiments, the kit is used for determining the likelihood of success of a specific treatment and/or selecting patient for the treatment.

Additional embodiments will be apparent to persons skilled in the relevant art based on the teachings contained herein.

DEFINITIONS

Figure 1:
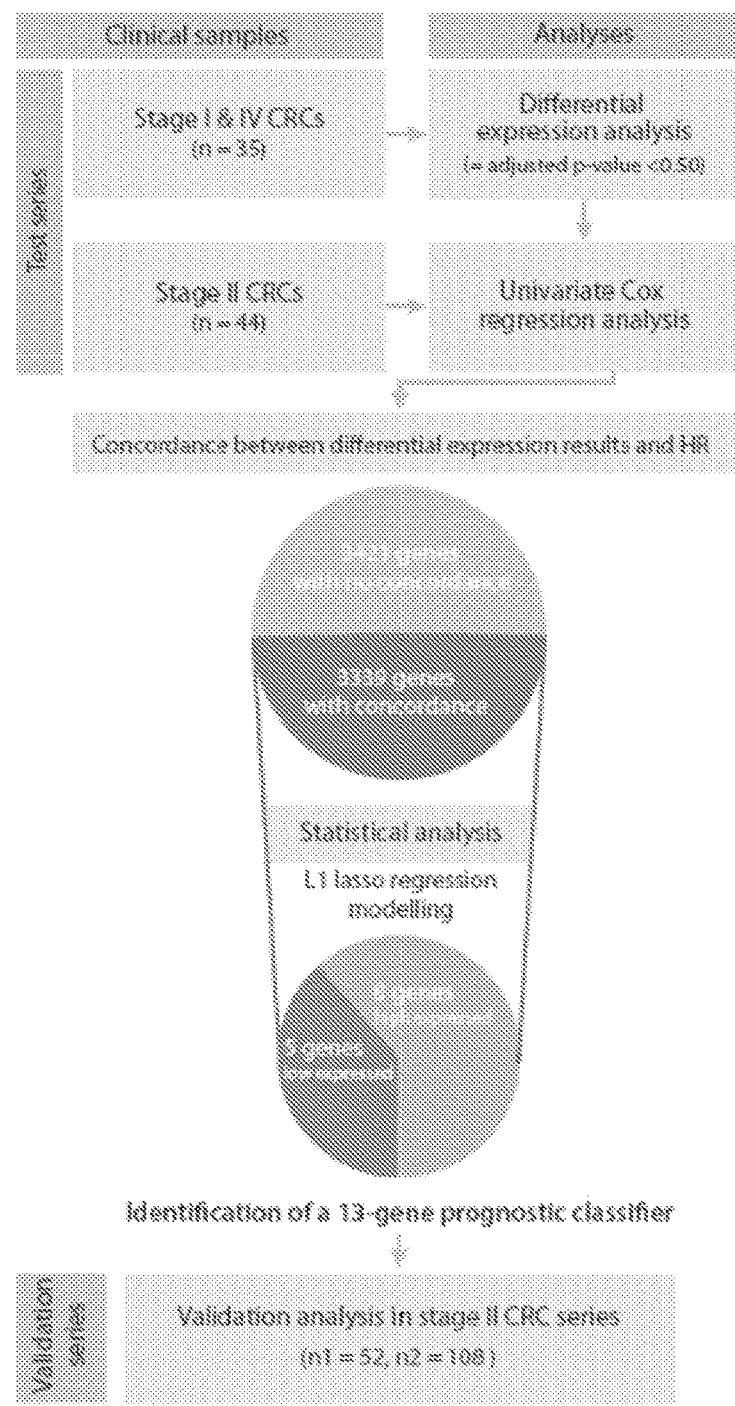
FIG. 1 describes gene selection criteria leading to identification of the prognostic gene expression classifier in the test series. From the initial list of 17,617 genes, 6,760 genes were differential expressed between stage I and IV tumours with a stage adjusted p-value <0.50, and 3,339 genes (49%) were common for the list of genes with differential expression between stage I and IV tumors, and the high and low expressed genes associated with high risk of relapse among stage II CRC patients. From these genes a 13-gene expression classifier was identified to indicate high-risk stage II CRC patients. The prognostic impact of this gene classifier was successfully validated in two independent sample series. Hazard ratio (HR) was obtained from univariate Cox regression analysis.

To facilitate an understanding of the present invention, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, the terms "colorectal cancer informative reagent" refers to a reagent or reagents that are informative for identification of expression of cancer gene markers described herein. In some embodiments, reagents are primers, probes or antibodies for detection of gene expression products (e.g., RNA transcripts or proteins) of the following genes: PIGR, CXCL13, MMP3, TUBA1B, SESN1, AZGP1, KLK6, EPHA7, SEMA3A, DSC3, CXCL10, ENPP3, BNIP3, PLA2G2A, GZMK, MMP1, AKD1, XRCC4 RAET1L, TTC30A, HAS2, CPE, CXCL9, GBP4, RPS6KA6, ENPP5, RAP1B, DYNLL1, and RPS27L.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. As used herein, the term "metastasized colorectal cancer cells" is meant to refer to colorectal cancer cells which have metastasized; colorectal cancer cells localized in a part of the body other than the colorectal.

As used herein, "an individual is suspected of being susceptible to metastasized colorectal cancer" is meant to refer to an individual who is at an above-average risk of developing metastasized colorectal cancer. Examples of individuals at a particular risk of developing colorectal cancer are those whose family medical history indicates above average incidence of colorectal cancer among family members and/or those who have already developed colorectal cancer and have been effectively treated who therefore face a risk of relapse and recurrence. Other factors which may contribute to an above-average risk of developing metastasized colorectal cancer which would thereby lead to the classification of an individual as being suspected of being susceptible to metastasized colorectal cancer may be based upon an individual's specific genetic, medical and/or behavioral background and characteristics.

The term "neoplasm" as used herein refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells. The term "colorectal neoplasm-specific marker" refers to any biological material that can be used to indicate the presence of a colorectal neoplasm (e.g., a premalignant colorectal neoplasm, a malignant colorectal neoplasm, a metastatic colorectal neoplasm). Examples of colorectal neoplasm-specific markers include, but are not limited to, the 13 gene signature described herein.

As used herein, the term "amplicon" refers to a nucleic acid generated using primer pairs. The amplicon is typically single-stranded DNA (e.g., the result of asymmetric amplification), however, it may be RNA or dsDNA.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specfic PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, etl al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N6-methyladenosine, aziridinylcytosine, pseudoisocytosine, 5-(carboxyhydroxyl-methyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

The term "locus" as used herein refers to a nucleic acid sequence on a chromosome or on a linkage map and includes the coding sequence as well as 5' and 3' sequences involved in regulation of the gene.

DETAILED DESCRIPTION OF THE INVENTION

The present invention relates to methods and biomarkers (e.g., gene expression biomarkers) for detection of colorectal cancer in biological samples (e.g., tissue samples, biopsy samples, stool samples, blood samples, plasma samples, serum samples). In some embodiments, methods and biomarkers of the present invention find use in detection of colon cancer and in providing a prognosis to colorectal cancer patients.

Molecular markers such as mutations in KRAS and BRAF, as well as chromosome and microsatellite instability (MSI) have been systematically analysed for prognostic potential in CRC. So far, only KRAS mutation analysis is implemented into clinical practice as a predictive marker for the effect of EGFR antibodies in metastatic disease. [7-10] Analysis of other known critical CRC genes are neither recommended for screening, nor used as prognostic and/or predictive markers. [11,12]

Several studies have identified gene expression signatures with prognostic impact in stage II and III CRC patients. [13-19] In early studies, small sample series and lack of validation in independent samples limited the powers of the drawn conclusions. However, recent publications have addressed these limitations and promising gene signatures have been suggested [13,14,17,18] although none of these were specifically targeting stage II CRC.

In this study we have improved risk stratification of stage II CRC patients. By applying high resolution exon-level microarrays to accurately determine gene expression levels, we have developed a gene classifier for prediction of relapse. The predictive value of this expression signature was validated across two patient series, populations and microarray generations.

Microarray technology have proven highly applicable in gaining insight into carcinogenesis.[28] In the present study, we used a high-resolution microarray with probes for each exon of each gene in the genome, combined with a stringent statistical approach to identify a high-risk stage II patient group. Two independent sample series were analyzed, generating robust gene expression measurements targeting genes along their full lengths. This may have contributed to the robustness of the signature presented here, which in addition to the clinically independent in-house sample series was validated in a third independent publicly available dataset. The samples in the latter series (validation series II) had been analyzed by a different type of expression microarray compared with the in-house data series, targeting primarily the 3' end of the genes. [13,14,18]

There is a risk of overfitting in survival modelling of high dimensional data characterized by a reduced significance of the predictor when applied to an independent data set. To address this challenge, a Cox proportional hazards model using L1 (lasso) penalization for optimal selection of genes, favoring selection of genes with strong prognostic value, high expression variances, and low correlation among each other, with the purpose of preventing overfitting was applied. [25,29,30] The lasso method has been described in a study on breast cancer [25]. This method and identified a 13-gene prognostic classifier of stage II CRCs which has been named "Cologuide".

Today, stage II patients are considered for adjuvant chemotherapeutic treatment if they are at a high risk of relapse based on clinical and pathological evaluation. According to ASCO recommendations, adverse factors include advanced T-stage, few examined lymph nodes, tumor perforation, and low tumor differentiation. [5] The high-risk patient group did not include those with pT4 stage or low grade tumors. This is in compliance with a recent study by Salazar and colleagues which showed a disconcordance in risk stratification between their signature and clinical risk factors, [17] underlining the need for additional molecular information to more precisely pinpoint patients with the least favorable outcome. MSI-status has also been shown to have associations with patient survival. [10] In this study, none of the MSI tumours (test series and validation series I) were categorized as high-risk samples according to the gene expression signature, in agreement with the favorable prognosis associated with MSI.

Initially in the process of reducing thousands of genes to an informative set for outcome in stage II patients, genes were identified with expression levels associated with metastatic capacity, e.g., those that distinguished between stage I and stage IV. Functional analysis of the genes supported their biological relevance (Table 7). Jorissen et al. used a similar approach comparing overlapping genes in different datasets to find prognostic subgroups for stage II and III CRC. [13] They did not apply any further statistical model for the identification of their prognostic signature, and thus, the resulting large number of genes (n=128) may complicate the transfer to a routine clinical test. [13] In our study, we aimed to identify a non-redundant set of genes to simplify such a transfer. Two assays, ColoPrint and Oncotype DX, have been launched to improve risk prediction in early stage CRC [31,32] with an 18 and 12-gene prognostic classifier, respectively. [17,33] The ColoPrint was limited to validation in only one internal data set, and the robustness of the signature is awaiting evaluation in a prospective trial. [34] The Oncotype DX 19 was not identified by a genome wide gene expression approach, but after analyses of a few hundred genes selected from the literature due to claimed prognostic value, [33,35] also calling for additional validation. [36] The test series in this study consisted of samples from a consecutive collection of CRC patients. Sixteen percent of stage II patients were identified as high-risk patients, comparing well with the survival rate in stage II patients. [2] A similarly sized subgroup was identified in both validation series I and II (13% and 16%, respectively). Generally, in other studies seeking prognostic stratification of stage II patients, a higher percentage of the patients have been categorized into poor prognosis groups ranging from 37-51%. [13,14,17,18] This probably reflects the different statistics used to classify patients. Validation series I was preselected to be enriched for stage II patients with recurrent disease (37% 5-year RFS). Hence, the identification of a high-risk profile in only 13% of the samples does not correctly represent the total relapse rate for these patients, but is a result of the use of the same stringent criteria for patient stratification in all three sample series (the 20th and 80th percentiles of expression values). The gene signature presented here convincingly holds prognostic information across three patient series. The "Cologuide"—stage II was identified by statistically means ensuring no or very low co-variation among the genes that constitute the classifier, an advantage when transferring a short gene list to a clinical test.

Evading immune surveillance and subsequent destruction has recently been suggested as a novel hallmark of cancer by Hanahan and Weinberg. [37] We have recently shown that the immunity index of CRC is striking and associated to age at disease onset. [38] Several of the genes in the presented "Cologuide" classifier are also related to the immune system, such as the chemokines, BNIP3, AZGP1, and ENPP3. Another interesting gene in the signature is KLK6, the homolog to KLK3, encoding the prostate-specific antigen (PSA) which is widely used as a detection and monitoring biomarker for prostate cancer. [39]

I. Diagnostic and Screening Methods

As described above, embodiments of the present invention provide diagnostic, prognositic and screening methods and kits that utilize the detection of altered levels of expression of cancer marker genes (e.g., PIGR, CXCL13, MMP3, TUBA1B, SESN1, AZGP1, KLK6, EPHA7, SEMA3A, DSC3, CXCL10, ENPP3, BNIP3, PLA2G2A, GZMK, MMP1, AKD1, XRCC4 RAET1L, TTC30A, HAS2, CPE, CXCL9, GBP4, RPS6KA6, ENPP5, RAP1B, DYNLL1, or RPS27L) and combinations thereof. In some embodiments, the methods and kits utilize or enable detection of altered gene expression in a subject of two or more, three or more, five or more, ten or more, 11 or more, 12 or more, or 13 cancer marker genes selected from one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the methods and kits utilize colorectal cancer informative reagents for the detection of a gene product (e.g., RNA transcript or protein or one or more, two or more, three or more, five or more, ten or more, 11 or more, 12 or more, or 13 cancer marker genes listed in column A of Table 1. In some embodiments, one or more of the cancer marker genes listed in column B of table 1 may be substituted for the corresponding cancer marker gene in column A and the appropriate colorectal cancer informative reagent may be utilized in the method or kit. Exemplary, non-limiting embodiments are described below.

TABLE 1

| Column A | Column B |
|---|---|
| PIGR | PLA2G2A |
| CXCL13 | GZMK |
| MMP3 | MMP1 |
| SESN1 | AKD1 |
| AZGP1 | XRCC4 |
| KLK6 | RAET1L |
| EPHA7 | TTC30A |
| SEMA3A | HAS2 |
| DSC3 | CPE |
| CXCL10 | CXCL9 |
| | GBP4 |
| ENPP3 | RPS6KA6 |
| BNIP3 | ENPP5 |
| TUBA1B | RAP1B |
| | DYNLL1 |
| | RPS27L |

Any patient sample suspected of containing the genes may be tested according to methods of embodiments of the present invention. By way of non-limiting examples, the sample may be tissue (e.g., a colorectal biopsy sample or other tissue sample), blood, stool or a fraction thereof (e.g., plasma, serum, etc.).

In some embodiments, the patient sample is subjected to preliminary processing designed to isolate or enrich the sample for the pseudogenes or cells that contain the pseudogenes. A variety of techniques known to those of ordinary skill in the art may be used for this purpose, including but not limited to: centrifugation; immunocapture; cell lysis; and, nucleic acid target capture (See, e.g., EP Pat. No. 1 409 727, herein incorporated by reference in its entirety).

While the present invention exemplifies several markers specific for detecting and providing a prognosis for colorectal cancer, any marker that is correlated with the presence or absence of colorectal cancer may be used, alone or in combination with the markers described herein. A marker, as used herein, includes, for example, nucleic acid(s) whose production or mutation or lack of production is characteristic of a colorectal neoplasm or a prognosis thereof. Depending on the particular set of markers employed in a given analysis, the statistical analysis will vary. For example, where a particular combination of markers is highly specific for colorectal cancer, the statistical significance of a positive result will be high. It may be, however, that such specificity is achieved at the cost of sensitivity (e.g., a negative result may occur even in the presence of colorectal cancer). By the same token, a different combination may be very sensitive (e.g., few false negatives), but has a lower specificity.

Particular combinations of markers may be used that show optimal function with different ethnic groups or sex, different geographic distributions, different stages of disease, different degrees of specificity or different degrees of sensitivity. Particular combinations may also be developed which are particularly sensitive to the effect of therapeutic regimens on disease progression. Subjects may be monitored after a therapy and/or course of action to determine the effectiveness of that specific therapy and/or course of action. Markers for other cancers, diseases, infections, and metabolic conditions are also contemplated for inclusion in a multiplex or panel format.

The methods are not limited to a particular type of mammal. In some embodiments, the mammal is a human. In some embodiments, the colorectal neoplasm is premalignant. In some embodiments, the colorectal neoplasm is malignant. In some embodiments, the colorectal neoplasm is colorectal cancer without regard to stage of the cancer (e.g., stage I, II, III, or IV). In some embodiments, the colorectal cancer is stage II.

A. DNA and RNA Detection—Colorectal Cancer Informative Reagents

Expression of the cancer marker genes of the present invention are detected using a variety of nucleic acid techniques known to those of ordinary skill in the art, including but not limited to: nucleic acid sequencing; nucleic acid hybridization; and nucleic acid amplification. These techniques utilize colorectal informative reagents such as nucleic acid probes and primers that hybridize to or can be used to amplify gene products of the cancer marker genes so that the level of expression of the respective cancer marker gene can be determined.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art, See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

In some embodiments, deep sequencing is utilized to provide an analysis of the sequence and frequency of RNA molecules in the samples. Suitable deep sequencing techniques include, but are not limited to, next generation sequencing techniques such as single molecule real time sequencing (Pacific Biosciences), sequencing by synthesis (Illumina, Inc.), 454 pyrosequencing (Roche Diagnostics, Inc.), SOLiD sequencing (Life Technologies, Inc.), and ion semiconductor sequencing (Life Technologies, Inc.).

2. Hybridization

Illustrative non-limiting examples of nucleic acid hybridization techniques include, but are not limited to, in situ hybridization (ISH), microarray, nuclease protection assay, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts (e.g., pseudogenes) within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, gene expression is detected using fluorescence in situ hybridization (FISH). In some embodiments, FISH assays utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present invention further provides a method of performing a FISH assay on human colorectal cells, human colorectal tissue or on the fluid surrounding said human colorectal cells or tissue. Specific protocols are well known in the art and can be readily adapted for the present invention. Guidance regarding methodology may be obtained from many references including: In situ Hybridization: Medical Applications (eds. G. R. Coulton and J. de Belleroche), Kluwer Academic Publishers, Boston (1992); In situ Hybridization: In Neurobiology; Advances in Methodology (eds. J. H. Eberwine, K. L. Valentino, and J. D. Barchas), Oxford University Press Inc., England (1994); In situ Hybridization: A Practical Approach (ed. D. G. Wilkinson), Oxford University Press Inc., England (1992)); Kuo, et al., Am. J. Hum. Genet. 49:112-119 (1991); Klinger, et al., Am. J. Hum. Genet. 51:55-65 (1992); and Ward, et al., Am. J. Hum. Genet. 52:854-865 (1993)). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121, 489 and 6,573,043. All of these references are hereby incorporated by reference in their entirety and may be used along with similar references in the art and with the information provided in the Examples section herein to establish procedural steps convenient for a particular laboratory.

In some embodiments, the present invention utilizes nuclease protection assays. Nuclease protection assays are useful for identification of one or more RNA molecules of known sequence even at low total concentration. The extracted RNA is first mixed with antisense RNA or DNA probes that are complementary to the sequence or sequences of interest and the complementary strands are hybridized to form double-stranded RNA (or a DNA-RNA hybrid). The mixture is then exposed to ribonucleases that specifically cleave only single-stranded RNA but have no activity against double-stranded RNA. When the reaction runs to completion, susceptible RNA regions are degraded to very short oligomers or to individual nucleotides; the surviving RNA fragments are those that were complementary to the added antisense strand and thus contained the sequence of interest. Suitable nuclease protection assays, include, but are not limited to those described in U.S. Pat. No. 5,770,370; EP 2290101A3; US 20080076121; US 20110104693; each of which is incorporated herein by reference in its entirety. In some embodiments, the present invention utilizes the quantitative nuclease protection assay provided by HTG Molecular Diagnostics, Inc. (Tuscon, Ariz.).

3. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., genes described herein) by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink jetprinting; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Nucleic acids (e.g., cancer marker genes) may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *Bio Technol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified nucleic acids can be detected by any conventional means. For example, the cancer marker genes described herein can be detected by hybridization with a detectably labeled probe and measurement of the resulting hybrids. Illustrative non-limiting examples of detection methods are described below.

One illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

In some embodiments, a TaqMan™ detection system is utilized to detect and quantify expression of the cancer marker genes. The TaqMan probe system relies on the 5'-3' exonuclease activity of Taq polymerase to cleave a dual-labeled probe during hybridization to the complementary target sequence and fluorophore-based detection. As in other real-time PCR methods, the resulting fluorescence signal permits quantitative measurements of the accumulation of the product during the exponential stages of the PCR; however, the TaqMan probe significantly increases the specificity of the detection. TaqMan probes consist of a fluorophore covalently attached to the 5'-end of the oligonucleotide probe and a quencher at the 3'-end. Several different fluorophores (e.g. 6-carboxyfluorescein, acronym: FAM, or tetrachlorofluorescein, acronym: TET) and quenchers (e.g. tetramethylrhodamine, acronym: TAMRA, or dihydrocyclopyrroloindole tripeptide minor groove binder, acronym: MGB) are available. The quencher molecule quenches the fluorescence emitted by the fluorophore when excited by the cycler's light source via FRET (Fluorescence Resonance Energy Transfer). As long as the fluorophore and the quencher are in proximity, quenching inhibits any fluorescence signals. TaqMan probes are designed such that they anneal within a DNA region amplified by a specific set of primers. As the Taq polymerase extends the primer and synthesizes the nascent strand (again, on a single-strand template, but in the direction opposite to that shown in the diagram, i.e. from 3' to 5' of the complementary strand), the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore. Hence, fluorescence detected in the real-time PCR thermal cycler is directly proportional to the fluorophore released and the amount of DNA template present in the PCR.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

Another illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

B. Protein Detection—Colorectal Cancer Informative Reagents

The cancer marker genes described herein may be detected as proteins using a variety of protein techniques known to those of ordinary skill in the art, including but not limited to: protein sequencing; and, immunoassays.

1. Sequencing

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined.

2. Immunoassays

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

II. Data Analysis

In some embodiments, a computer-based analysis program is used to translate the raw data generated by the detection assay (e.g., the expression level a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or stool sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., prognosis of disease free survival or metastasis) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

III. Compositions & Kits

Compositions for use in the diagnostic methods described herein include, but are not limited to, kits comprising one or more colorectal cancer informative reagents as described above. In some embodiments, the kits comprise one or more colorectal cancer informative reagents for detecting altered gene expression in a sample from a subject having or suspected of having colorectal cancer of one or more two or more, five or more, 10 or more, 11 or more, 12 or more or 13 genes selected from the group consisting of one of (PIGR or PLA2G2A), one of (CXCL13 or GZMK), one of (MMP3 or MMP1), one of (TUBA1B, RAP1B, DYNLL1, or RPS27L), one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (CXCL10, CXCL9 or GBP4), one of (ENPP3 or RPS6KA6), and one of (BNIP3 or ENPP5). In some embodiments, the kits contain colorectal cancer informative reagents specific for a cancer gene marker, in addition to detection reagents and buffers. In preferred embodiments, the colorectal informative reagent is a probe(s) that specifically hybridizes to a respective gene product(s) of the one or more genes, a set(s) of primers that amplify a respective gene products) of the one or more genes, an antigen binding protein(s) that binds to a respective gene product(s) of the one or more genes, or a sequencing primer(s) that hybridizes to and allows sequencing of a respective gene products) of the one or more genes. The probe and antibody compositions of the present invention may also be provided in the form of an array. In preferred embodiments, the kits contain all of the components necessary to perform a detection assay, including all controls, directions for performing assays, and any necessary software for analysis and presentation of results.

In some embodiments, the kits include instructions for using the reagents contained in the kit for the detection and characterization of cancer in a sample from a subject. In some embodiments, the instructions further comprise the statement of intended use required by the U.S. Food and Drug Administration (FDA) in labeling in vitro diagnostic products. The FDA classifies in vitro diagnostics as medical devices and requires that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use. Where applicable, photographs or engineering drawings should be supplied; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; 8) Any additional information regarding the in vitro diagnostic product requested that is necessary for the FDA to make a substantial equivalency determination. Additional information is available at the Internet web page of the U.S. FDA.

III. Methods of Use

As disclosed herein, the present invention provides colorectal cancer informative reagents and methods for determining a prognosis of colorectal cancer in a subject, diagnosing a colorectal cancer in a subject, predicting a predisposition to colorectal cancer in a subject, predicting the likelihood of recurrence of colorectal cancer in a subject, or selecting a subject with a disease for treatment with a particular therapy. The colorectal cancer can be stage I, II, III, or IV colorectal cancer. In some preferred embodiments, embodiments of the present invention provide compositions and methods for providing a prognosis to a patient diagnosed with colorectal cancer (e.g., stage II colorectal cancer). For example, in some embodiments, altered expression relative to a control sample (e.g., non-cancerous colorectal tissue or stage I or IV colorectal cancer) of one or more of PIGR, CXCL13, MMP3, TUBA1B, SESN1, AZGP1, KLK6, EPHA7, SEMA3A, DSC3, CXCL10, ENPP3, and BNIP3 is associated with a poor prognosis. In particular, in some embodiments, a decreased level of expression of one or more of one of (PIGR or PLA2G2A), one of (CXCL13 or GZMK), one of (MMP3 or MMP1), one of (TUBA1B, RAP1B, DYNLL1, or RPS27L), and one of (CXCL10, CXCL9 or GBP4) relative to a reference level of expression in a control sample and/or an increased level of expression of one or more of one of (SESN1 or AKD1), one of (AZGP1 or XRCC4), one of (KLK6 or RAET1L), one of (EPHA7 or TTC30A), one of (SEMA3A or HAS2), one of (DSC3 or CPE), one of (ENPP3 or RPS6KA6), and one of (BNIP3 or ENPP5) relative to a reference level of expression in a control sample of the genes is associated with a poor prognosis (e.g., decreased survival or increased risk of metastasis). In some embodiments, the reference level is from a subject diagnosed with stage I or IV colorectal cancer. In some embodiments, the reference level is from a subject not diagnosed with colorectal cancer. In some embodiments, the level of expression as compared to the reference level is indicative of a poor prognosis. In some embodiments, the poor prognosis is a decreased chance of survival. In some embodiments, the poor prognosis is an increased chance of recurrence or metastasis of colorectal cancer. In some embodiments, the prognosis is the likelihood of 5 year relapse free survival.

In some embodiments, the prognostic information is used to determine a treatment course of action for the subject. For example, in some embodiments, subjects found to have a poor prognosis can be given adjuvant chemotherapy, while subjects with a good prognosis can be treated with surgery alone. In further embodiments, the assays of the present invention are utilized during clinical testing of therapeutic agents for colorectal cancer. It is contemplated that the assays for gene products as described above will define specific patient populations for which treatment with the therapeutic agent is more or less effective than the patient population as a whole. Thus, in some embodiments of the present invention, methods are provided where subjects are screened using the assays of the present invention and patients with a particular profile of gene expression as described above are selected for treatment with a particular therapeutic agent or therapeutic regime.

EXPERIMENTAL

The following examples are provided in order to demonstrate and further illustrate certain preferred embodiments and aspects of the present invention and are not to be construed as limiting the scope thereof.

Example 1

Materials and Methods
Patients and Tumour Samples

Altogether 315 CRCs from three independent patient series were analysed for global gene expression, comprising a test series and two validation series (I and II).

The test series consisted of 112 fresh frozen primary CRC samples (stage I-IV) from an equal number of patients consecutively collected at Oslo University Hospital, Aker, Norway between 2005 and 2008. The median follow-up time for survivors was 47 months (range 32-61 months). Adjuvant chemotherapy was given according to Norwegian guidelines and none of the patients had received preoperative radiotherapy. The series included 44 stage II and 33 stage III patients. All underwent curative resection and no bowel perforation was reported. Validation series I consisted of 52 stage II and 43 stage III CRC samples collected from hospitals in the Oslo region during the period 1987-89. None of the patients had received adjuvant chemotherapy, which was introduced as standard treatment for stage III patients under 75 years in Norway in 1997. The median follow-up time was 71 months (range 4-120 months). For both series tumor stage was determined according to guidelines from The International Union Against Cancer (UICC)/American Joint Committee on Cancer (AJCC). MSI status has previously been reported for both series. [20,21] A detailed description of the two in-house sample series is summarized in table 4.

Raw data has been deposited to the Gene Expression Omnibus (GEO) public repository for microarray data (accession number GSE24550, GSE29638, and GSE30378). Accession numbers for all samples included in the present study are listed in table 5.

External Validation Series

Validation series II consisted of gene expression data from 108 stage II CRC samples, accessed from the GEO (GSE14333 and GSE17538). The clinical samples were from USA and Australia and according to the GEO entries, none of the patients had received chemo- or radiotherapy preoperatively. Available clinicopathological data are summarized in table 4. By correlation analyses of the probe cell intensity (CEL) files, we found overlapping samples from the Moffit Cancer Centre in the two datasets. The non-overlapping samples (n=108) were combined to get a validation series with a substantial number of stage II tumors. [13,14,18] Samples included in the present study are listed in table 5.

Sample Preparation and Gene Expression Analysis

Tissue was taken from each tumor, rapidly frozen in liquid nitrogen and stored at −80° C. until processing. Prior to RNA isolation, a tissue section was taken from each sample, stained by hematoxylin and eosin, and evaluated by a pathologist for tumor cell content. RNA was isolated using the DNA/RNA Mini Kit (QIAGEN, Hilden, Germany) as recommended by the manufacturer. Quantity and quality measurements were carried out by using UV spectroscopy (NanoDrop ND-100, Thermo Fisher Scientific, Waltham, Mass., USA) and Agilent 2100 Bioanalyzer (Agilent Technologies, Santa Clara, Calif., USA).

For gene expression measurements, GeneChip® Human Exon 1.0 ST Arrays (Affymetrix, Santa Clara, Calif., USA) with more than 5 million features and approximately 1.4 million probe sets were used. One µg total RNA was used as input to a ribosomal RNA reduction reaction, (RiboMinus™ Human/Mouse Transcriptome Isolation kit, Life Technologies, Carlsbad, Calif., USA), followed by cDNA synthesis, amplification, and DNA sense strand labelling according to the GeneChip® Whole Transcript (WT) Sense Target Labeling Assay Manual (Affymetrix). Each 11 sample was hybridized for 16 to 18 hours and washed, stained, and scanned as recommended in the manual. For each sample, a CEL file storing intensity measures was generated by the Affymetrix GeneChip® Command Console software (version 1.0). These files were further processed through background correction, quantile normalization, and summarization at the gene level by Robust Multichip Analysis (RMA) using the Affymetrix® Expression Console software (HuEx-1_0-st-v2.r2 gene-core library file). The HuEx-1_0-st-v2.na31.hg19.transcript.csv annotation file identified 17,617 annotated genes.

Samples from the GSE14333 and GSE17538 datasets were analysed on Affymetrix HGU133 Plus2.0 arrays. CEL files from stage II patients were downloaded and analysed by RMA using the Affymetrix® Expression Console software. The HG-U133_Plus_2.cdf and HGU133_Plus_2.na31.annot.csv files were used as library and annotation files, respectively.

Development of the Gene Expression Signature

Prior to multivariate survival modelling, the gene expression dataset from the test series was filtered to enrich for genes with potential prognostic predictive value. Initially, univariate hazard ratios (HR) were calculated from the 44 stage II CRCs (Cox regression analyses; 5-year relapsefree survival (RFS) where relapses or death from same cancer were defined as an event). This analysis was performed using the weighted correlation network analysis (WGCNA) software package [22,23] for the R computing environment. Genes with metastasis associated expression were identified by analyses of the 23 stage I and 12 stage IV CRC samples from the same biobank as the test series (empirical Bayes moderated t-statistics implemented in the Limma software package run with R). [24] A false discovery rate (FDR) was calculated for each gene and only genes with an adjusted p-value less than 0.50 were included in the downstream analyses (n=6,760 genes). Only genes showing concordance between the direction of expression regulation from stage I to IV tumors (up or down-regulated in stage IV), and associations with patient survival at high or low expression levels in stage II tumors (as indicated by the HR) were retained (n=3,339 genes; FIG. 1). The R commands used for the analyses are listed in table 6.

The expression levels for this filtered set of 3,339 genes were used as input for multivariate survival modelling of the test series' stage II tumours (risk of relapse) using L1 penalized (lasso) estimation in the Cox proportional hazards model. [25,26] A likelihood cross validation method was used to calculate the number of genes with non-zero regression coefficients as a function of the tuning parameter lambda ($\lambda 1$). The optimal $\lambda 1$-value from crossvalidation corresponded to zero genes. We chose to reduce the stringency of the penalization ($\lambda 1$) to systematically increase the number of genes with non-zero regression coefficients in a stepwise manner. The first 15 optimal gene sets were identified by this approach. All samples were on a gene-by-gene basis given positive prognostic scores indicative of high risk of relapse whenever their expression were above the 80th or below the 20th percentile (depending on whether high or low expression was associated with high risk of relapse, respectively). The number of genes associated with a high risk of relapse was summarized for all samples using each possible signature from 1 to 15 genes. We specifically selected signatures with at least 10% of the samples in the high risk of relapse group. P-values (Wald statistics) were calculated for each signature to identify the one with strongest association with RFS.

Validation of the Gene Expression Signature

The optimal prognostic signature identified in the test series was further subjected to validation in both validation series. Stage II CRC samples within each series were categorized into a low or high risk of relapse group based on the number of genes exceeding the 80th and 20th percentile levels of each gene in the signature. The expression data in validation series II was derived from Affymetrix HG-U133 Plus2.0 microarrays, and for genes targeted by multiple probe sets, the median expression from the well annotated probe sets were used further (excluding probesets with low specificity, annotated with "_x_at").

Statistics

Kaplan Meier survival analyses with log rank test were used to estimate 5-year RFS where relapse or death from CRC were defined as events, and patients were censored at last follow-up, death from other cancer, non-cancer death, or treatment-related death within five years. Survival data from validation series II were indicated as disease-free survival and according to their publication, [13,18] relapse of disease were defined as an event and hence, in compliance with our definition. In Cox proportional hazard regression models Wald statistics were used to calculate the p-values in both univariate and multivariate Cox regression analyses. In the multivariate analyses all parameters were entered into a forward stepwise model for all clinical and molecular parameters. A p-value less than 0.05 were considered statistically significant. PASW 18.0 (SPSS Inc., Chicago, Ill.) was used in Kaplan Meier and Cox regression analyses. Partek Genomics Suite (version 6.5, Partek Incorporated, MI) was used to calculate correlation coefficients (Pearson) between samples and gene expression data. Functional enrichment analyses were performed by the Database for annotation, visualization and integrated discovery (DAVID), [27] and known pathways defined by the Kyoto Encyclopedia of Genes and Genomes (KEGG) were included in the analyses. Enriched KEGG pathways with modified Fisher's Exact p-values less than 0.05 were considered statistically significant.

Results

Stepwise Identification of a Prognostic Gene Expression Signature for Stage II CRC The initial list of 17,617 genes was filtered based on expression data from the test series, enriching for the 3,339 genes with metastasis associated expression changes (stage IV versus stage I) and accordingly associated with prognosis (stage IV-like expression in stage II poor survivors), and thus more likely to identify a robust prognostic classifier (see Materials and methods). Subsequently, by lasso penalized multivariate Cox proportional hazards analyses, prognostic gene expression signatures ranging in size from 1 to 15 genes were identified (at reduced stringency of the penalty). Based on a threshold at the 80th and 20th percentiles of the gene expression measures, the samples were divided into low and high risk of relapse groups for each signature.

Figure 3:
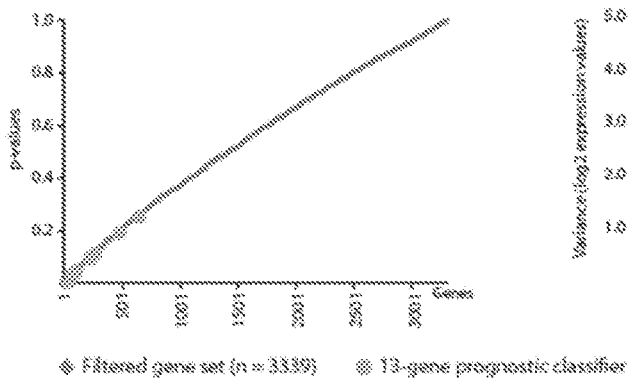
FIG. 3 shows that the 13-gene prognostic classifier, identified from the 44 stage II CRC in the test series by the lasso penalization method, favors identification of genes with a clear association to survival (A), high variance (B) and low correlation to each other (C), as shown in the figure. (A) P-values generated from univariate Cox regression analysis (see Material and Methods) were on average significantly lower compared with the P-values from the 3,339 genes taken into the analysis ($p=0.07$ versus $p=0.55$, respectively). (B) Calculation of the gene expression variance also shows that the average variance of the 13 genes is higher than for the gene set (variance 2.39 versus 0.23, respectively). (C) The heatmap shows a low correlation between the 13 genes (range $-0.37<r<0.44$) with the exception of CXCL10 and CXCL13, both localized at chromosome band 4q21, with a correlation coefficient at $r=0.70$.
Figure 3:
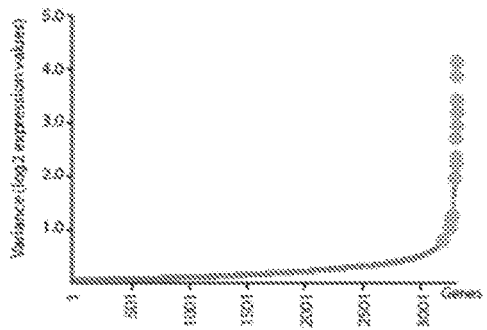
Figure 3:
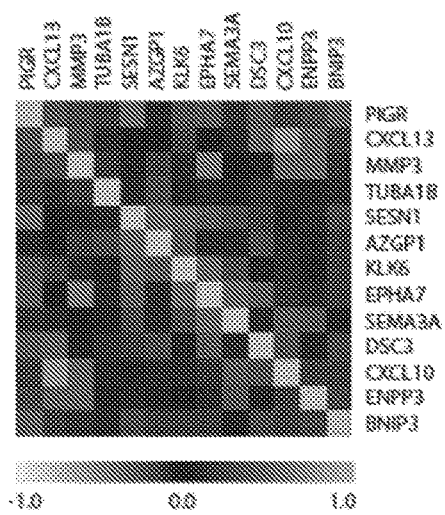

The prognostic gene expression signatures were ranked based on predictive performance in the test series (p-values) for the actual number of genes associated with poor survival, and a 13-gene expression signature was identified as optimal. The ranking of the combinations of gene expression signatures revealed that at least five or more genes with a positive prognostic score were needed to separate the patients with a low risk of relapse from patients with a high risk of relapse. Poor prognosis was associated with low expression of the genes PIGR, CXCL13, MMP3, TUBA1B, and CXCL10 and high expression of SESN1, AZGP1, KLK6, EPHA7, SEMA3A, DSC3, ENPP3, and BNIP3 (table 1). According to the applied lasso penalized algorithm for variable selection, the identified genes were highly associated to survival, as well as showing a high variance and low degree of correlation in the gene expression when compared to the genes applied into the analysis (FIG. 3).

Figure 2:
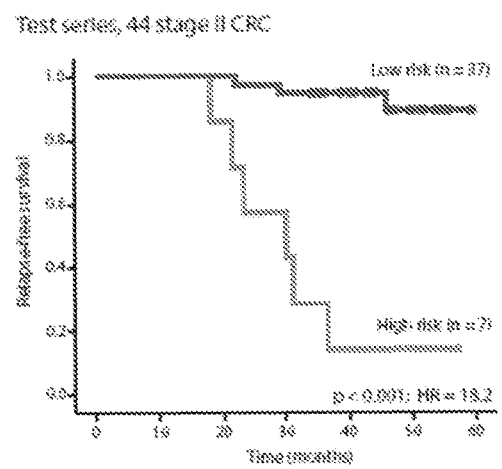
FIG. 2 shows Kaplan Meier survival curves illustrating relapse-free survival (RFS) among stage II CRC patients. (A) In the test series, the two risk of relapse groups are well separated ($p<0.001$). (B) and (C) In both validation series I and II (b and c, respectively), the prognostic gene expression classifier identifies a low and high risk of relapse groups with statistically significance ($p=0.02$ and $p=0.001$, respectively).
Figure 2:
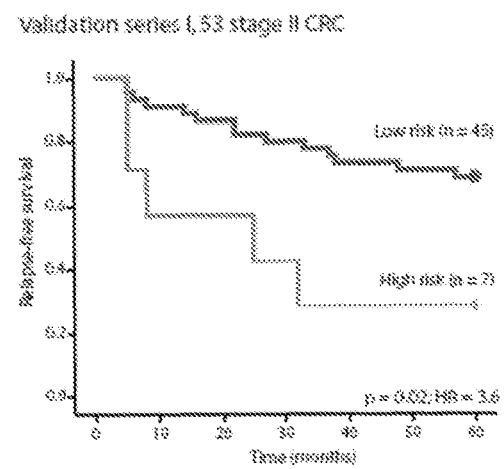
Figure 2:
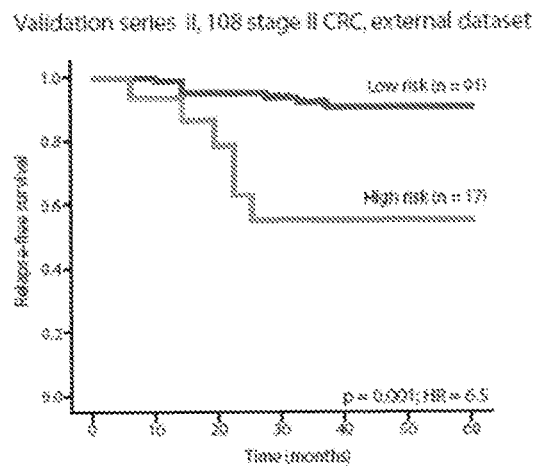

In the test series, 16% of the patients were identified as having a high risk of relapse and their 5-year RFS rate was 14% as compared to 89% in those patients identified with a low risk of relapse (FIG. 2A; table 2; p<0.001; HR=18.2). Validation of the Gene Expression Signature in Two Independent Sample Series of Stage II CRC Samples In validation series I, 13% of the patients were assigned a high risk of relapse. There was a statistically significant difference between the low and high-risk group (69% versus 29% 5-year RFS, respectively; FIG. 2B; table 2; p=0.02; HR=3.6). For these patients, 10-year follow-up time was available. The difference in survival rates between the risk groups remained statistically significant also after ten years (p=0.02; HR=3.1).

Stage II CRC samples in validation series II were used as an external and independent validation series for the 13-gene prognostic expression signature. These patients were collected from a different population than the in-house datasets, and analyzed on a different version of the Affymetrix microarrays. High-risk patients in this series had a 55% 5-year RFS rate compared to 91% in the low risk patients (FIG. 2C; table 2; p=0.001; HR=6.5).

Associations Between the 13-Gene Prognostic Classifier and Clinical Parameters

To assess whether the prognostic signature was a strong prognostic classifier independent of various clinicopathological features, clinical data was included in both uni- and multivariate Cox regression analyses (table 2). In univariate analyses, the prognostic signature was the strongest variable associated with prognosis in both the test series and validation series I. Patients who had received adjuvant chemo- and/or radiotherapy in validation series II, had poorer outcome compared to those who had not received treatment (p=0.02; HR=3.7). In multivariate analyses, the prognostic signature was in all three sample series an independent prognostic classifier (table 2; p<0.004; multivariate HR>5.1). There were no associations between risk stratification according to the 13-gene classifier and the different clinical and molecular parameters in the three series (table 3).

Specificity for Stage II Tumors

Figure 4:
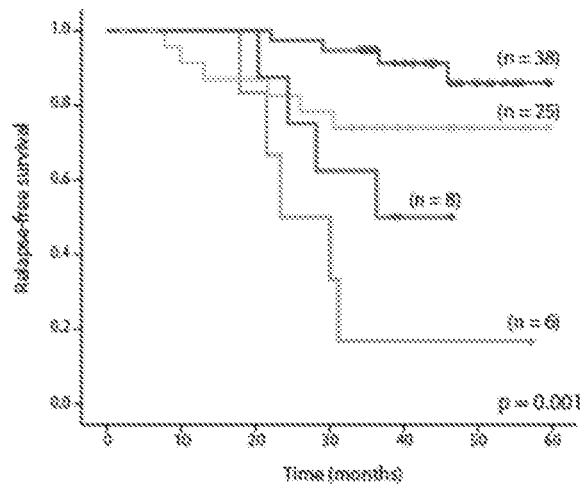
FIG. 4 shows Stage II and III CRC samples and survival probability calculated by the use of the 13-gene expression classifier. In both the test series (A) and validation series I (B) the prognostic gene expression classifier enabled significant separation according to prognostic outcome only for stage II patients.
Figure 4:
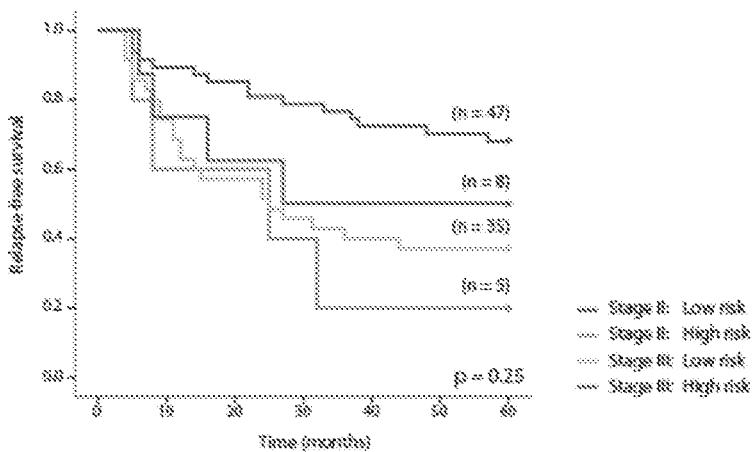

To investigate whether the 13-gene prognostic classifier for stage II CRC also could identify stage III patients with poor prognosis, the prognostic score was recalculated including both stage II and III samples. As expected, the stage II samples in the test series were separated into low and high risk of relapse groups whereas the signature could not separate the stage III samples (FIG. 4A). Samples in validation series I were collected before adjuvant chemotherapy became standard treatment of stage III in Norway, and thereby patients in this sample series were not influenced by the treatment benefit. Nevertheless, only stage II samples were significantly separated into low and high-risk groups (FIG. 4B).

TABLE 1

Identities of the 13 genes in the prognostic expression signature and their univariate associations to prognosis

| Transcript cluster ID* | Gene symbol† | Gene name† | Chromosome location† | Gene expression level and association to poor prognasis |
|---|---|---|---|---|
| 2453006 | PIGR | polymeric immunoglobulin receptor | 1q31-q41 | low |
| 2732508 | CXCL13 | chemokine (C—X—C motif) ligand 13 | 4q21 | low |
| 3388830 | MMP3 | matrix metallopeptidase 3 (stromelysin 1, progelatinase) | 11q22.3 | low |
| 3453732 | TUBA1B | tubulin, alpha 1b | 12q13.12 | low |
| 2968652 | SESN1 | sestrin 1 | 6q21 | high |
| 3063589 | AZGP1 | alpha-2-glycoprotein 1, zinc-binding | 7q22.1 | high |
| 3868768 | KLK6 | kallikrein-related peptidase 6 | 19q13.3 | high |
| 2965206 | EPHA7 | EPH receptor A7 | 6q16.3 | high |
| 3059464 | SEMA3A | sema domain, immunoglobulin domain (Ig), short basic domain, secreted, (semaphorin) 3A | 7p12.1 | high |
| 3802924 | DSC3 | desmocollin 3 | 18q12.1 | high |
| 2773958 | CXCL10 | chemokine (C—X—C motif) ligand 10 | 4q21 | low |
| 2925871 | ENPP3 | ectonucleotide pyrophosphatase/phosphodiesterase 3 | 6q22 | high |
| 3314040 | BNIP3 | BCL2/adenovirus E1B 19 kDa interacting protein 3 | 10q26.3 | high |

*Affymetrix GeneChip® Human Exon 1.0 ST Arrays transcript cluster ID.
†Approved by the HUGO Gene

TABLE 2

Univariate and multivariate Cox regression analysis (5-year RFS) of the 13-gene prognostic signature and clinical factors in stage II CRC samples from the test series and validation series I and II

| Parameters | No. of patients | Univariate P-value* | Univariate HR (95% CI) | Multivariate P-value† | Multivariate HR (95% CI) |
|---|---|---|---|---|---|
| Training series (n = 44) | | | | | |
| Prognostic signature | | | | | |
| Low risk (ref)/high risk | 37/7 | <0.001 | 18.2 (4.5-74.1) | <0.001 | 61.8 (8.7-440.0) |
| Age | | | | | |
| Continuous | 44 | 0.16 | 0.1 (0.9-1.0) | | |
| Gender | | | | | |
| Female (ref)/male | 30/14 | 0.74 | 1.3 (0.3-5.1) | | |
| Tumour localization | | | | | |
| Colon (ref)/rectum | 40/4 | — | — | | |
| No. of lymph nodes examined | | | | | |
| n < 12 (ref)/n ≥ 12 | 5/39 | 0.99 | 1.0 (0.1-8.2) | | |
| MSI status | | | | | |
| Instable (ref)/stable | 9/35 | 0.44 | 2.3 (0.3-18.3) | | |
| Adjuvant chemo-/radiotherapy | | | | | |
| No (ref)/yes | 40/4 | — | — | | |
| Validation series I (n = 52) | | | | | |
| Prognostic signature | | | | | |
| Low risk (ref)/high risk | 45/7 | 0.02 | 3.6 (1.3-10.1) | 0.001 | 6.4 (2.1-19.6) |
| Age | | | | | |
| Continuous | 52 | 0.07 | 1.0 (1.0-1.1) | 0.01 | 1.1 (1.0-1.1) |
| Gender | | | | | |
| Female (ref)/male | 30/22 | 0.68 | 1.2 (0.5-3.0) | | |
| Tumour localization | | | | | |
| Colon (ref)/rectum | 32/20 | 0.75 | 0.9 (0.3-2.2) | | |
| MSI status | | | | | |
| Instable (ref)/stable/NA | 2/49/1 | — | — | | |
| Validation series II (n = 108) | | | | | |
| Prognostic signature | | | | | |
| Low risk (ref)/high risk | 91/17 | 0.001 | 6.5 (2.2-19.7) | 0.004 | 5.1 (1.7-15.5) |
| Age | | | | | |
| continuous | 108 | 0.20 | 1.0 (0.9-1.0) | | |
| Gender | | | | | |
| Female (ref)/male | 48/60 | 0.65 | 0.8 (0.3-2.3) | | |
| Tumour localization | | | | | |
| Colon (ref)/rectum | 96/12 | 0.15 | 2.6 (0.7-9.4) | | |
| Adjuvant chemo-/radiotherapy | | | | | |
| No (ref)/yes/NA | 72/22/14 | 0.02 | 3.7 (1.3-11.1) | 0.04 | 3.3 (1.1-9.9) |

*P-values calculated from Wald statistics: statistically significant p-values (<0.05) in bold. P-values and HR were not calculated whenever there were less than five samples in either of the groups.
†In the multivariate analyses, only p-

TABLE 3

13-gene prognostic signature and associations to clinical parameters in stage II CRC Samples

| Parameters | Training series (n = 44) | | | Validation series I (n = 52) | | | Validation series II (n = 100) | | |
|---|---|---|---|---|---|---|---|---|---|
| | Low-risk group | High-risk group | P-value* | Low-risk group | High-risk group | P-value* | Low-risk group | High-risk group | P-value* |
| No. of patients | 37 | 7 | | 45 | 7 | | 91 | 17 | |
| Age | | | | | | | | | |
| Mean | 75 | 73 | 0.76 | 67 | 62 | 0.31 | 68 | 65 | 0.55 |
| Gender | | | | | | | | | |
| Female | 26 | 4 | 0.66 | 26 | 4 | 1.00 | 41 | 7 | 0.80 |
| Male | 11 | 3 | | 19 | 3 | | 50 | 10 | |
| Tumour localization | | | | | | | | | |
| Colon | 34 | 6 | 0.51 | 26 | 6 | 0.23 | 82 | 14 | 0.40 |
| Rectum | 3 | 1 | | 19 | 1 | | 9 | 3 | |
| Grade | | | | | | | | | |
| High | 3 | 0 | 1.00 | — | — | | — | — | |
| Moderate | 32 | 7 | | — | — | | — | — | |
| Low | 2 | 0 | | — | — | | — | — | |
| T stage | | | | — | — | | — | — | |
| T3 | 35 | 7 | 1.00 | — | — | | — | — | |
| T4 | 2 | 0 | | — | — | | — | — | |
| No. of lymph nodes examined | | | | | | | | | |
| <12 | 4 | 1 | 1.00 | | | | | | |
| ≥12 | 33 | 6 | | | | | | | |
| MSI status | | | | | | | | | |
| MSI | 9 | 0 | 0.31 | 2 | 0 | 1.00 | — | — | |
| MSS | 28 | 7 | | 42 | 7 | | — | — | |
| NA | | | | 1 | | | | | |
| Adjuvant chemo-/radiotherapy | | | | | | | | | |
| No | 33 | 7 | 1.00 | 45 | 7 | | 60 | 12 | 0.54 |
| Yes | 4 | 0 | | | | | 17 | 5 | |

*P-values for age were calculated by t-test and by the Fisher's Exact test for all other parameters CI, confidence interval; HR, hazard ratio; MSI, microsatellite instability; MSS, microsatellite stability; NA, information not available.

TABLE 4

Summary of patient clinicopathological information of the test and validation series

| Parameters | Test series* | Validation series I* | Validation series II† |
|---|---|---|---|
| Number of samples | 112 | 95 | 108 |
| Stage | | | |
| Stage I | 23 | — | — |
| Stage II | 44 | 52 | 108 |
| Stage III | 33 | 43 | — |
| Stage IV | 12 | — | — |
| Age median, year (range) | 72 (30-93) | 66 (24-87) | 70 (30-94) |
| Mean follow-up time, months (range) | | | |
| All stages | 47 (33-61)‡ | 71 (4-120)** | 42 (0.4-119)** |
| Samples with 5-year RFS | | | |
| Stage II | 9 | 19 | 13 |
| Stage III | 10 | 27 | |
| Gender | | | |
| Female | 62 | 49 | 48 |
| Male | 52 | 46 | 60 |
| Localization | | | |
| Colon | 92 | 58 | 96 |
| Rectum | 20 | 37 | 12 |
| Grade | | | |
| High grade | 6 | — | — |
| Medium grade | 95 | — | — |
| Low grade | 9 | — | — |
| NA | 2 | — | — |
| T stage | | | |
| T1 | 5 | — | — |
| T2 | 19 | — | — |
| T3 | 82 | — | — |
| T4 | 6 | — | — |

TABLE 4-continued

Summary of patient clinicopathological information of the test and validation series

| Parameters | Test series* | Validation series I* | Validation series II† |
|---|---|---|---|
| N stage | | | |
| N0 | 68 | — | — |
| N1 | 28 | — | — |
| N2 | 16 | — | — |
| Number of lymph node examined†† | | | |
| <12 | 5 | — | — |
| ≥12 | 39 | — | — |
| Adjuvant chemo-/radiotherapy | | | |
| No | 82 | 95 | 99 |
| Yes | 30 | — | 9 |
| NA | — | — | 14 |

*Samples from in-house biobank.
†Samples retrieved from GEO datasets GSE14333 and GSE17538.
‡Follow-up time includes only survivors from disease.
**Follow-up time includes time to relapse or time to death/last followup.
††Only stage II.
NA, information not available;
RFS, relapse-free survival.

TABLE 5

GSE data set accession number and GEO sample identification of all samples included in the study

| GEOdataset | GEOsampleID | Sample series |
|---|---|---|
| GSE24550 | GSM712398 | Test series |
| GSE24550 | GSM712399 | Test series |
| GSE24550 | GSM712400 | Test series |
| GSE24550 | GSM712401 | Test series |
| GSE24550 | GSM712402 | Test series |
| GSE24550 | GSM712403 | Test series |
| GSE24550 | GSM712404 | Test series |
| GSE24550 | GSM712405 | Test series |
| GSE24550 | GSM712406 | Test series |
| GSE24550 | GSM712407 | Test series |
| GSE24550 | GSM712408 | Test series |
| GSE24550 | GSM712409 | Test series |
| GSE24550 | GSM712410 | Test series |
| GSE24550 | GSM712411 | Test series |
| GSE24550 | GSM712412 | Test series |
| GSE24550 | GSM712413 | Test series |
| GSE24550 | GSM712414 | Test series |
| GSE24550 | GSM712415 | Test series |
| GSE24550 | GSM712416 | Test series |
| GSE24550 | GSM712417 | Test series |
| GSE24550 | GSM712418 | Test series |
| GSE24550 | GSM712419 | Test series |
| GSE24550 | GSM712420 | Test series |
| GSE24550 | GSM712421 | Test series |
| GSE24550 | GSM712422 | Test series |
| GSE24550 | GSM712423 | Test series |
| GSE24550 | GSM712424 | Test series |
| GSE24550 | GSM712425 | Test series |
| GSE24550 | GSM712426 | Test series |
| GSE24550 | GSM712427 | Test series |
| GSE24550 | GSM712428 | Test series |
| GSE24550 | GSM712429 | Test series |
| GSE24550 | GSM712430 | Test series |
| GSE24550 | GSM712431 | Test series |
| GSE24550 | GSM712432 | Test series |
| GSE24550 | GSM712433 | Test series |
| GSE24550 | GSM712434 | Test series |
| GSE24550 | GSM712435 | Test series |
| GSE24550 | GSM712436 | Test series |
| GSE24550 | GSM712437 | Test series |
| GSE24550 | GSM712438 | Test series |
| GSE24550 | GSM712439 | Test series |
| GSE24550 | GSM712440 | Test series |
| GSE24550 | GSM712441 | Test series |
| GSE24550 | GSM712442 | Test series |
| GSE24550 | GSM712443 | Test series |
| GSE24550 | GSM712444 | Test series |
| GSE24550 | GSM712445 | Test series |
| GSE24550 | GSM712446 | Test series |
| GSE24550 | GSM712447 | Test series |
| GSE24550 | GSM712448 | Test series |
| GSE24550 | GSM712449 | Test series |
| GSE24550 | GSM712450 | Test series |
| GSE24550 | GSM712451 | Test series |
| GSE24550 | GSM712452 | Test series |
| GSE24550 | GSM712453 | Test series |
| GSE24550 | GSM712454 | Test series |
| GSE24550 | GSM712455 | Test series |
| GSE24550 | GSM712456 | Test series |
| GSE24550 | GSM712457 | Test series |
| GSE24550 | GSM712458 | Test series |
| GSE24550 | GSM712459 | Test series |
| GSE24550 | GSM712460 | Test series |
| GSE24550 | GSM712461 | Test series |
| GSE24550 | GSM712462 | Test series |
| GSE24550 | GSM712463 | Test series |
| GSE24550 | GSM712464 | Test series |
| GSE24550 | GSM712465 | Test series |
| GSE24550 | GSM712466 | Test series |
| GSE24550 | GSM712467 | Test series |
| GSE24550 | GSM712468 | Test series |
| GSE24550 | GSM712469 | Test series |
| GSE24550 | GSM712470 | Test series |
| GSE24550 | GSM712471 | Test series |
| GSE24550 | GSM712472 | Test series |
| GSE24550 | GSM712473 | Test series |
| GSE24550 | GSM712474 | Test series |
| GSE29638 | GSM751135 | Test series |
| GSE29638 | GSM734430 | Test series |
| GSE29638 | GSM734431 | Test series |
| GSE29638 | GSM734432 | Test series |
| GSE29638 | GSM734433 | Test series |
| GSE29638 | GSM734434 | Test series |
| GSE29638 | GSM734435 | Test series |
| GSE29638 | GSM734436 | Test series |
| GSE29638 | GSM751136 | Test series |
| GSE29638 | GSM751137 | Test series |
| GSE29638 | GSM734437 | Test series |
| GSE29638 | GSM734438 | Test series |
| GSE29638 | GSM751138 | Test series |
| GSE29638 | GSM751139 | Test series |
| GSE29638 | GSM734439 | Test series |
| GSE29638 | GSM751140 | Test series |
| GSE29638 | GSM734440 | Test series |
| GSE29638 | GSM734441 | Test series |
| GSE29638 | GSM734444 | Test series |
| GSE29638 | GSM734446 | Test series |
| GSE29638 | GSM734450 | Test series |
| GSE29638 | GSM734451 | Test series |
| GSE29638 | GSM734452 | Test series |
| GSE29638 | GSM734454 | Test series |
| GSE29638 | GSM734456 | Test series |
| GSE29638 | GSM734457 | Test series |
| GSE29638 | GSM734459 | Test series |
| GSE29638 | GSM734461 | Test series |
| GSE29638 | GSM734462 | Test series |
| GSE29638 | GSM734463 | Test series |
| GSE29638 | GSM734464 | Test series |
| GSE29638 | GSM734465 | Test series |
| GSE29638 | GSM734466 | Test series |
| GSE29638 | GSM734469 | Test series |
| GSE29638 | GSM751141 | Test series |
| GSE30378 | GSM712082 | Validation series I |
| GSE30378 | GSM712083 | Validation series I |
| GSE30378 | GSM712084 | Validation series I |

TABLE 5-continued

GSE data set accession number and GEO sample identification of all samples included in the study

| GEOdataset | GEOsampleID | Sample series |
|---|---|---|
| GSE30378 | GSM712085 | Validation series I |
| GSE30378 | GSM712086 | Validation series I |
| GSE30378 | GSM712087 | Validation series I |
| GSE30378 | GSM712088 | Validation series I |
| GSE30378 | GSM712089 | Validation series I |
| GSE30378 | GSM712090 | Validation series I |
| GSE30378 | GSM712091 | Validation series I |
| GSE30378 | GSM712092 | Validation series I |
| GSE30378 | GSM712093 | Validation series I |
| GSE30378 | GSM712094 | Validation series I |
| GSE30378 | GSM712095 | Validation series I |
| GSE30378 | GSM712096 | Validation series I |
| GSE30378 | GSM712097 | Validation series I |
| GSE30378 | GSM712098 | Validation series I |
| GSE30378 | GSM712099 | Validation series I |
| GSE30378 | GSM712100 | Validation series I |
| GSE30378 | GSM712101 | Validation series I |
| GSE30378 | GSM712102 | Validation series I |
| GSE30378 | GSM712103 | Validation series I |
| GSE30378 | GSM712104 | Validation series I |
| GSE30378 | GSM712105 | Validation series I |
| GSE30378 | GSM712106 | Validation series I |
| GSE30378 | GSM712107 | Validation series I |
| GSE30378 | GSM712108 | Validation series I |
| GSE30378 | GSM712109 | Validation series I |
| GSE30378 | GSM712110 | Validation series I |
| GSE30378 | GSM712111 | Validation series I |
| GSE30378 | GSM712112 | Validation series I |
| GSE30378 | GSM712113 | Validation series I |
| GSE30378 | GSM712114 | Validation series I |
| GSE30378 | GSM712115 | Validation series I |
| GSE30378 | GSM712116 | Validation series I |
| GSE30378 | GSM712117 | Validation series I |
| GSE30378 | GSM712118 | Validation series I |
| GSE30378 | GSM712119 | Validation series I |
| GSE30378 | GSM712120 | Validation series I |
| GSE30378 | GSM712121 | Validation series I |
| GSE30378 | GSM712122 | Validation series I |
| GSE30378 | GSM712123 | Validation series I |
| GSE30378 | GSM712124 | Validation series I |
| GSE30378 | GSM712125 | Validation series I |
| GSE30378 | GSM712126 | Validation series I |
| GSE30378 | GSM712127 | Validation series I |
| GSE30378 | GSM712128 | Validation series I |
| GSE30378 | GSM712129 | Validation series I |
| GSE30378 | GSM712130 | Validation series I |
| GSE30378 | GSM712131 | Validation series I |
| GSE30378 | GSM712132 | Validation series I |
| GSE30378 | GSM712133 | Validation series I |
| GSE30378 | GSM712134 | Validation series I |
| GSE30378 | GSM712135 | Validation series I |
| GSE30378 | GSM712136 | Validation series I |
| GSE30378 | GSM712137 | Validation series I |
| GSE30378 | GSM712138 | Validation series I |
| GSE30378 | GSM712139 | Validation series I |
| GSE30378 | GSM712140 | Validation series I |
| GSE30378 | GSM712141 | Validation series I |
| GSE30378 | GSM712142 | Validation series I |
| GSE30378 | GSM712143 | Validation series I |
| GSE30378 | GSM712144 | Validation series I |
| GSE30378 | GSM712145 | Validation series I |
| GSE30378 | GSM712146 | Validation series I |
| GSE30378 | GSM712147 | Validation series I |
| GSE30378 | GSM712148 | Validation series I |
| GSE30378 | GSM712149 | Validation series I |
| GSE30378 | GSM712150 | Validation series I |
| GSE30378 | GSM712151 | Validation series I |
| GSE30378 | GSM712152 | Validation series I |
| GSE30378 | GSM712153 | Validation series I |
| GSE30378 | GSM712154 | Validation series I |
| GSE30378 | GSM712155 | Validation series I |
| GSE30378 | GSM712156 | Validation series I |
| GSE30378 | GSM712157 | Validation series I |
| GSE30378 | GSM712158 | Validation series I |
| GSE30378 | GSM712159 | Validation series I |
| GSE30378 | GSM712160 | Validation series I |
| GSE30378 | GSM712161 | Validation series I |
| GSE30378 | GSM712162 | Validation series I |
| GSE30378 | GSM712163 | Validation series I |
| GSE30378 | GSM712164 | Validation series I |
| GSE30378 | GSM753769 | Validation series I |
| GSE30378 | GSM753770 | Validation series I |
| GSE30378 | GSM753771 | Validation series I |
| GSE30378 | GSM753772 | Validation series I |
| GSE30378 | GSM753773 | Validation series I |
| GSE30378 | GSM753774 | Validation series I |
| GSE30378 | GSM753775 | Validation series I |
| GSE30378 | GSM753776 | Validation series I |
| GSE30378 | GSM753777 | Validation series I |
| GSE30378 | GSM753778 | Validation series I |
| GSE30378 | GSM753779 | Validation series I |
| GSE30378 | GSM753780 | Validation series I |
| GSE14333 | GSM358385 | Validation series II |
| GSE14333 | GSM358386 | Validation series II |
| GSE14333 | GSM358387 | Validation series II |
| GSE14333 | GSM358388 | Validation series II |
| GSE14333 | GSM358389 | Validation series II |
| GSE14333 | GSM358390 | Validation series II |
| GSE14333 | GSM358391 | Validation series II |
| GSE14333 | GSM358392 | Validation series II |
| GSE14333 | GSM358393 | Validation series II |
| GSE14333 | GSM358394 | Validation series II |
| GSE14333 | GSM358395 | Validation series II |
| GSE14333 | GSM358396 | Validation series II |
| GSE14333 | GSM358397 | Validation series II |
| GSE14333 | GSM358398 | Validation series II |
| GSE14333 | GSM358399 | Validation series II |
| GSE14333 | GSM358400 | Validation series II |
| GSE14333 | GSM358401 | Validation series II |
| GSE14333 | GSM358402 | Validation series II |
| GSE14333 | GSM358403 | Validation series II |
| GSE14333 | GSM358404 | Validation series II |
| GSE14333 | GSM358405 | Validation series II |
| GSE14333 | GSM358406 | Validation series II |
| GSE14333 | GSM358407 | Validation series II |
| GSE14333 | GSM358408 | Validation series II |
| GSE14333 | GSM358409 | Validation series II |
| GSE14333 | GSM358410 | Validation series II |
| GSE14333 | GSM358411 | Validation series II |
| GSE14333 | GSM358412 | Validation series II |
| GSE14333 | GSM358413 | Validation series II |
| GSE14333 | GSM358414 | Validation series II |
| GSE14333 | GSM358415 | Validation series II |
| GSE14333 | GSM358416 | Validation series II |
| GSE14333 | GSM358417 | Validation series II |
| GSE14333 | GSM358418 | Validation series II |
| GSE14333 | GSM358419 | Validation series II |
| GSE14333 | GSM358420 | Validation series II |
| GSE14333 | GSM358421 | Validation series II |
| GSE14333 | GSM358422 | Validation series II |
| GSE14333 | GSM358423 | Validation series II |
| GSE14333 | GSM358424 | Validation series II |
| GSE14333 | GSM358425 | Validation series II |
| GSE14333 | GSM358426 | Validation series II |
| GSE14333 | GSM358427 | Validation series II |
| GSE14333 | GSM358428 | Validation series II |
| GSE14333 | GSM358429 | Validation series II |
| GSE14333 | GSM358430 | Validation series II |
| GSE14333 | GSM358431 | Validation series II |
| GSE14333 | GSM358432 | Validation series II |
| GSE14333 | GSM358433 | Validation series II |
| GSE14333 | GSM358434 | Validation series II |
| GSE14333 | GSM358435 | Validation series II |
| GSE14333 | GSM358436 | Validation series II |
| GSE14333 | GSM358437 | Validation series II |
| GSE14333 | GSM358438 | Validation series II |
| GSE14333 | GSM358439 | Validation series II |
| GSE14333 | GSM358440 | Validation series II |
| GSE14333 | GSM358441 | Validation series II |
| GSE14333 | GSM358442 | Validation series II |

TABLE 5-continued

GSE data set accession number and GEO sample identification of all samples included in the study

| GEOdataset | GEOsampleID | Sample series |
|---|---|---|
| GSE14333 | GSM358443 | Validation series II |
| GSE14333 | GSM358444 | Validation series II |
| GSE14333 | GSM358445 | Validation series II |
| GSE14333 | GSM358446 | Validation series II |
| GSE14333 | GSM358447 | Validation series II |
| GSE14333 | GSM358448 | Validation series II |
| GSE14333 | GSM358449 | Validation series II |
| GSE14333 | GSM358450 | Validation series II |
| GSE14333 | GSM358451 | Validation series II |
| GSE14333 | GSM358452 | Validation series II |
| GSE14333 | GSM358453 | Validation series II |
| GSE14333 | GSM358454 | Validation series II |
| GSE14333 | GSM358455 | Validation series II |
| GSE14333 | GSM358456 | Validation series II |
| GSE14333 | GSM358457 | Validation series II |
| GSE14333 | GSM358458 | Validation series II |
| GSE14333 | GSM358459 | Validation series II |
| GSE14333 | GSM358460 | Validation series II |
| GSE14333 | GSM358461 | Validation series II |
| GSE14333 | GSM358462 | Validation series II |
| GSE14333 | GSM358463 | Validation series II |
| GSE14333 | GSM358464 | Validation series II |
| GSE14333 | GSM358465 | Validation series II |
| GSE14333 | GSM358466 | Validation series II |
| GSE14333 | GSM358467 | Validation series II |
| GSE14333 | GSM358468 | Validation series II |
| GSE14333 | GSM358469 | Validation series II |
| GSE14333 | GSM358470 | Validation series II |
| GSE14333 | GSM358471 | Validation series II |
| GSE14333 | GSM358472 | Validation series II |
| GSE14333 | GSM358473 | Validation series II |
| GSE14333 | GSM358474 | Validation series II |
| GSE14333 | GSM358475 | Validation series II |
| GSE14333 | GSM358476 | Validation series II |
| GSE14333 | GSM358477 | Validation series II |
| GSE14333 | GSM358478 | Validation series II |
| GSE17538 | GSM437270 | Validation series II |
| GSE17538 | GSM437272 | Validation series II |
| GSE17538 | GSM437278 | Validation series II |
| GSE17538 | GSM437281 | Validation series II |
| GSE17538 | GSM437287 | Validation series II |
| GSE17538 | GSM437288 | Validation series II |
| GSE17538 | GSM437291 | Validation series II |
| GSE17538 | GSM437298 | Validation series II |
| GSE17538 | GSM437299 | Validation series II |
| GSE17538 | GSM437306 | Validation series II |
| GSE17538 | GSM437307 | Validation series II |
| GSE17538 | GSM437313 | Validation series II |
| GSE17538 | GSM437323 | Validation series II |
| GSE17538 | GSM437324 | Validation series II |

SUPPLEMENTARY TABLE 3

Overview of software packages and essential R commands used in the analyses

| Analysis | Software package | Input data | Commands |
|---|---|---|---|
| Identification of differentially expressed genes | Biobase* affy limma | Gene expression data from training series stage I and IV CRCs | #ExpressionSet, group = factor (targets$stage, levels = c("stage I", "stageIV"))<br>#design = model.matrix(~0 + group)<br>>fm1<-lmFit(ExpressionSet.design)<br>>contrast.matrix<-makeContrasts(stageIV-stageI, levels = design)<br>>fm2<-contrasts.fit(fm1, contrast.matrix)<br>>fm3<-eBayes(fm2)<br>>ttestLimma <- topTable(fm3, genelist = fm3$genes, coef = "stageIV-stageI", number = X, adjust method = "fdr", p-value = 1,lfo = 0) |
| Univariate Cox regression method | WGCNA | Gene expression data from training series stage II CRCs | # time, time to recurrence or censoring for each sample; event, 1 = recurrence, 0 = censoring for each sample; datExpt, created a matrix file from tab-delimited gene expression data with sample headings and first column with probe set id's (datExpr.txt)<br>>datExpr<-t(as. matrix(read.table("datExpr.txt",header = TRUE,sep = "t",row.names = 1, as is = TRUE))<br>>c<-standardScreeningCensoredTime(time, event, datExpr, fastCalculation = F) |
| L1 penalty (Lasso) and cross-validation to find optimal lambda | penalized | Gene expression data from training series stage II CRCs | # time, time to recurrence or censuring for each sample; event, 1 = recurrence, 0 = censoring for each sample; datExpr, created a matrix file from tab-delimited gene expression data with sample headings and first column with probe set id's (datExpr.txt)<br>>datExpt<-t(as.matrix(read.table("datExpr.txt",header = TRUE,sep = "t",row.names = 1.as.is = TRUE)))<br>>opt<-optL1(time,event,penalized = datExpr.fold = 10)<br>>opt<br>>coefficients(opt$fullfit)<br>#Commands to plot the profile of the cross-validated likelihood values and to check that an optimal λ1 is found<br>>prof<-profL1(time,event,penalized = datExpr.fold = opt$fold.steps = 20)<br>>plot(prof$lambda,prof$cvLtype = "1") |

SUPPLEMENTARY TABLE 3-continued

Overview of software packages and essential R commands used in the analyses

| Analysis | Software package | Input data | Commands |
|---|---|---|---|
| | | | #A single lasso fit predicting survival; X, chosen λ1<br>>pen<-penalized(s,penalized = d,lambda1 = X)<br>>show(pen)<br>>coefficients(pen) |

*To create the expression data set we used the Biobase software package from the Bioconductor project

TABLE 6

Functional analysis and significant KEGG pathways

| KEGG pathway term | | Count* | Fold Enrichment | P-value† | Gene List‡ |
|---|---|---|---|---|---|
| hsa04360 | Axon guidance | 39 | 1.8 | <0.001 | PLXNB1, MAPK3, SEMA3F, NGEF, NTN4, PAK4, EPHA7, SRGAP1, RASA1, RAC1, EPHA3, ITGB1, PAK3, PLXNA2, EFNA3, NFAT5, CDK5, SEMA6D, NTNG1, FIN, SEMA6C, SEMA3A, SEMA5A, CHP2, EFNA1, EPHA5, GNAI1, LIMK2, EFNA4, NTN3, CXCL12, PAK2, PTK2, DPTYSL5, EFNB1, EPHA8, SEMA4C, SEMA5B, PLXNA3 |
| hsa04310 | West signaling pathway | 41 | 1.6 | 0.003 | WNT8B, RBX1, LRP5, MAPK9, WNT8A, RAC1, FZD1, PPP2CB, MAPK10, WNT9B, PPP285A, PLCB1, PSEN1, AXTN1, LEF1, CAMK2B, NFAT5, DVL3, PRKACA, WNT2B, DKK1, FOSL1, PRICKLE2, WNT3A, SOXI7, MAPK8, CAMK2A, WLS, MAP3K7, DVL1, NKD1, PRICKLE1, CHP2, CER1, WNT16, LRP6, APC, WNT9A, WNT6, PPP2R1A, CTNNB1 |
| hsa05217 | Basal cell carcinoma | 19 | 2.0 | 0.004 | HHIP, WNT8B, DVL1, WNT8A, BMP4, FZD1, PTCH2, SMO, WNT9B, AXIN1, LEF1, DVL3, WNT16, APC, WNT9A, WNT2B, WNT6, WNT3A, CTNNB1 |
| hsa05200 | Pathways in cancer | 75 | 1.3 | 0.006 | E2F2, MAPK3, EPAS1, HHIP, RUNX1, RB1, FZD1, WNT9B, FGF9, ITGB1, AXIN1, LEF1, ARNT, CDK6, XLAP, PIK3CA, STAT1, TGFBR2, MAPK8, FASLG, LAMA4, WLS, FGF13, ACVR1B, WNT16, COL4A4, APC, ITGA3, PTK2, WNT9A, WNT6, BRAF, RARA, PDGFRA, CDK4, FGF4, STAT5B, RAF1, WNT8B, RBX1, PPARG, TGFB2, BID, LAMC2, MAPK9, WNT8A, VEGFA, BMP4, RAC1, PTCH2, MLH1, MAPK10, LAMB1, DVL3, NKX3-1, WNT2B, DAPK2, PLAS3, WNT3A, LAMC1, LAMB3, DVL1 CDKN2B, FOS, SMO, AKT2, RARB, CASP9, TPM3, PLD1, FGF8, CDH1, PIK3CB, CTNNB1, BIRC5 |
| hsa05210 | Colorectal cancer | 25 | 1.7 | 0.006 | PDGFRA, MAPK3, RAF1, TGFB2, MAPK9, RAC1, FZD1, MLH1, MAPK10, AXIN1, LEF1, DVL3, TGFBB2, PIK3CA, MAPK3, DVL1, FOS, ACVR1B, AKT2, CASP9, APC, BRAF, PIK3CB, CTNNB1, BIRC3 |
| hsa04510 | Focal adhesion | 49 | 1.4 | 0.009 | RBMS1, MAPK3, COMP, DOCK1, PAK4, ITGB1, PDPK1, XLAP, CAV1, PIK3CA, MAPK8, LAMA4, GRLF1, ACTN2, CAV2, COL11A2, ITGA3, COL4A4, PTK2, PAK2, TNR, ITGB6, BRAF, PDGFRA, MYLPF, RAF1, MYLK, VEGFA, MAPK9, LAMC2, RAC1, MYL9, LAMB1, MAPK10, MYL10, PAK3, CAPN2, ACTN1, FYN, ACTG1, ARHGAP5, ITGB5, LAMC1, LAMB3, AKT2, PDGFD, PDGFC, VAV3, PIK3CB, CTNNB1 |
| hsa04340 | Hedgehog signaling pathway | 18 | 1.9 | 0.011 | BMP8A, IHH, HHIP, WNT8B, WNT8A, BMP4, PTCH2, SMO, WNT9B, WNT16, ZIC2, WNT9A, PRKACA, LRP2, WNT2B, WNT6, WNT3A, DHH |
| hsa04660 | T cell receptor signaling pathway | 29 | 1.6 | 0.014 | CDK4, MAPK3, RAF1, PAK4, MAPK9, LCK, CD247, IFNG, MAP2K7, PAK3, NFAT5, CD8A, CD3D, FYN, PIK3CA, IL4, DLG1, CARD11, MAP3K7, FOS, ZAP70, AKT2, GRAP2, ICOS, CHP2, CTLA4, PAK2, VAV3, PIK3CB |

TABLE 6-continued

Functional analysis and significant KEGG pathways

| KEGG pathway term | | Count* | Fold Enrichment | P-value† | Gene List‡ |
|---|---|---|---|---|---|
| hsa05212 | Pancreatic cancer | 21 | 1.7 | 0.017 | E2F2, MAPK8, CDK4, MAPK3, RAF1, TGFB2, VEGFA, MAPK9, RB1, RAC1, ACVR1B, AKT2, CASP9, MAPK10, PLD1, CDK6, BRAF, PIK3CB, TGFBR2, STAT1, PIK3CA |
| hsa04350 | TGF-beta signaling pathway | 24 | 1.6 | 0.020 | BMP8A, COMP, SMAD2, MAPK3, RBX1, SMURF1, TGFB2, INHBE, BMPR2, CDKN2B, GDF7, ACVR2A, BMP4, ACVR1B, IFNG, PPP2CB, FST, CHRD, ACVR2B, AMH, TGFBR2, ACVR1, ACVRL1, PPP2R1A |
| hsa03320 | PPAR signaling pathway | 20 | 1.7 | 0.021 | CD36, PCK2, PCK1, PPARG, EHHADH, APOC3, GK3P, ADIPOQ, FABP2, CYP27A1, SORBS1, PDPK1, ACAA1, UCP1, PLTP, PPARA, ACSL3, LPL, ACADL, HMGCS2 |
| hsa04142 | Lysosome | 29 | 1.4 | 0.039 | GLB1, TBC1D24, AP4S1, CTSD, ATP6V1H, GBAP1, HEXB, SCARB2, GALC, CTSA, MAN2B1, ATP6V0A2, SMPD1, MANBA, GBA, CTSF, SGSH, GUSB, HGSNAT, FUCA1, LAMP2, CLN5, ATP6V0D1, LAPTM4A, ATP6V0A1, ATP6AP1, SORT1, PTPN14, LAMP1, CTSZ |
| hsa00511 | Other glycan degradation | 7 | 2.5 | 0.044 | MAN2B2, GLB1, GBA, MAN2B1, MANBA, GBAPI, HEXB, FUCA1 |
| hsa00590 | Arachidonic acid metabolism | 16 | 1.7 | 0.048 | HPGDS, GPX6, PLA2G2E, ALOX15, ALOX12, AKR1C3, PLA2G12A, PLA2G2D, CYP4F3, GGT7, PLA2G3, LTC4S, GPX2, PTGS1, CYP2B6, CYP2C9 |

*Number of genes involved in the KEGG pathway term.
†Moderated Fisher's Exact p-value.
‡Genes involved in the term.

Example 2

This example describes the confirmation of the microarray results using real-time quantitation of gene expression using a TaqMan™ assay as well as identification of genes that can be substituted for genes in the original 13 gene panel. ColoGuideEx was developed by expression data from Affymetrix microarrays (GeneChipR Human Exon 1.0 ST), and the transferrability to other gene expression platforms has been demonstrated by analysing the same genes in 19 stage II colorectal cancer samples by both microarrays and by real-time RT-PCR. A prognostic score was developed for the thirteen genes, where 15 of the 19 samples grouped into the same dichotomous groups as the original microarray-based ColoGuideEx. This is not intended to be the final RT-PCR-based classifier, but a crude model set up for the first 19 selected samples to demonstrate the feasibility of the RT-PCR-based approach as such, and the general robustness of ColoGuideEx in terms of transferrability to other expression platforms.

Briefly, TaqMan™ primers and probes were selected and tested for the 13 gene panel, and assay identifiers are provided in Table 7.

TABLE 7

| Gene Symbol | TaqMan Assay ID |
|---|---|
| PIGR | Hs00922561_m1 |
| CXCL13 | Hs00757930_m1 |
| MMP3 | Hs00968308_m1 |
| SESN1 | Hs00902787_m1 |
| AZGP1 | Hs00426651_m1 |
| KLK6 | Hs00160519_m1 |
| EPHA7 | Hs00177891_m1 |
| SEMA3A | Hs00173810_m1 |

TABLE 7-continued

| Gene Symbol | TaqMan Assay ID |
|---|---|
| DSC3 | Hs00170032_m1 |
| CXCL10 | Hs01124251_g1 |
| ENPP3 | Hs01038393_m1 |
| BNIP3 | Hs00969291_m1 |

Figure 5:
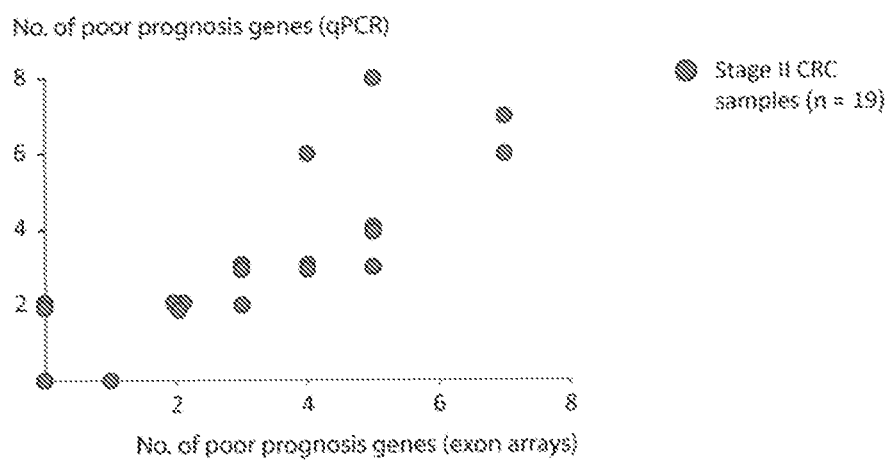
FIG. 5 provides a plot demonstrating the correlation of microarray data with TaqMan™ assay results for the 13 gene panel.
Figure 6:
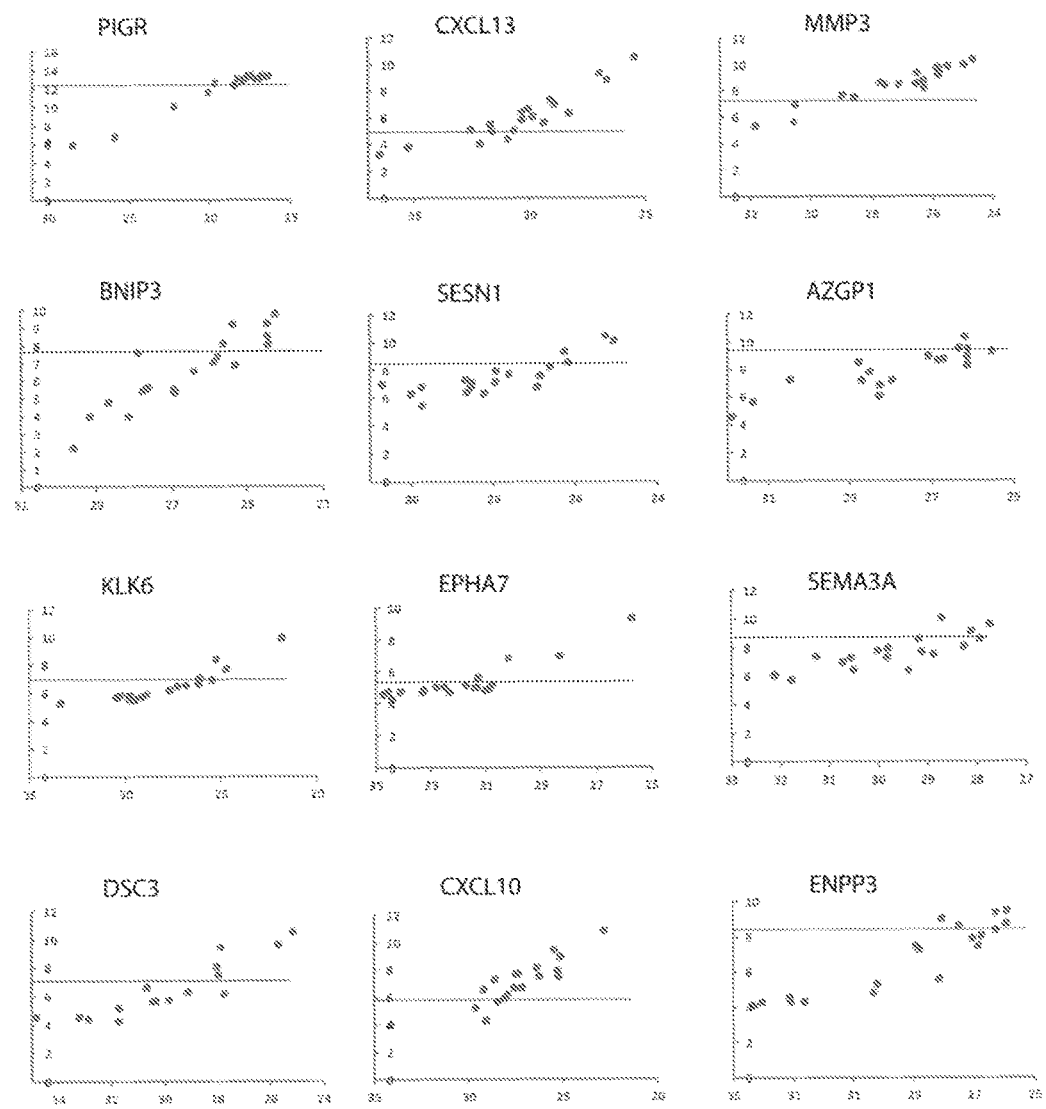
FIG. 6 provides plots for individual genes demonstrating the correlation of microarray data with quantitative RT-PCR (TaqMan™) assay results.

The reagents were used to analyze gene expression levels in patient samples. The results are presented in FIG. 5. This plot shows a good correspondence between TaqMan quantitative RT-PCR and the microarray data in the sample-wise number of genes in ColoGuideEx being expressed at levels associated with poor prognosis. Plots for individual genes are provided in FIG. 6. Since only a subset of the samples has been analyzed with qPCR at present (n=19 stage II samples), the thresholds for designating gene expression levels as associated with poor prognosis are not final. In the classification presented here, expression level thresholds for the qPCR data was set to classify the same amount of samples with poor prognosis per gene as for the microarray data. For example, PIGR expression by microarrays classified the 5 (of 19) samples with lowest expression as having poor prognosis. Accordingly, the 5 samples with lowest expression by qPCR were also classified as poor prognosis for this gene. Classification of patients with poor prognosis when expressing 5 or more of the 13 genes in ColoGuideEx at levels associated with poor prognosis (the threshold used in the publication of ColoGuideEx), results in classification of 15 of the 19 patients (79%) to the same category by qPCR and microarray data.

Expression levels of each of the 13 genes were assessed by TaqMan assays, and Pearson correlation coefficients between microarray and RT-PCR data are shown in Table 8 alongside with associated p-values. For 12 of the 13 genes, Pearson correlation had r>0.8 and p-values <0.0001.

TABLE 8

| | Gene | Pearson correlation coefficient (r) | p-value |
|---|---|---|---|
| ColoGuideEx (19 stage II samples from one patient series) | PIGR | −0.98 | 1.22E−13 |
| | CXCL13 | −0.91 | 9.38E−08 |
| | MMP3 | −0.96 | 9.49E−11 |
| | SESN1 | −0.84 | 8.15E−06 |
| | AZGP1 | −0.86 | 2.85E−06 |
| | KLK6 | −0.91 | 5.04E−08 |
| | EPHA7 | −0.88 | 5.81E−07 |
| | SEMA3A | −0.80 | 4.13E−05 |
| | DSC3 | −0.90 | 3.87E−07 |
| | CXCL10 | −0.88 | 8.86E−07 |
| | ENPP3 | −0.91 | 4.19E−08 |
| | BNIP3 | −0.90 | 1.18E−07 |

In additional experiments, the microarray data were analyzed to identify genes that could be substituted into the panel. Table 9 provides the results, listing the pairwise correlated genes, and their corresponding Pearson correlation coefficients (r) and associated significant levels (p-value), for two separate independent clinical sample sets.

TABLE 9

| | | 44 stage II AUS2 | | 52 stage II GIM | |
|---|---|---|---|---|---|
| ColoGuideEx | Backup gene | Corr coeff (r) | p value | Corr coeff (r) | p value |
| PIGR | PLA2G2A | 0.522 | 2.78E−04 | 0.543 | 3.26E−05 |
| CXCL13 | GZMK | 0.750 | 4.69E−09 | 0.773 | 1.97E−11 |
| MMP3 | MMP1 | 0.855 | 1.46E−13 | 0.857 | 5.51E−16 |
| SESN1 | AKD1 | 0.607 | 1.24E−05 | 0.557 | 1.80E−05 |
| AZGP1 | XRCC4 | 0.540 | 1.55E−04 | 0.501 | 1.57E−04 |
| KLK6 | RAET1L | 0.618 | 7.91E−06 | 0.471 | 4.31E−04 |
| EPHA7 | TTC30A | 0.420 | 4.50E−03 | 0.455 | 7.06E−04 |
| SEMA3A | HAS2 | 0.560 | 7.69E−05 | 0.700 | 7.68E−09 |
| DSC3 | CPE | 0.344 | 2.21E−02 | 0.336 | 1.49E−02 |
| CXCL10 | CXCL9 | 0.913 | 6.14E−18 | 0.893 | 5.57E−19 |
| | GBP4 | 0.838 | 1.25E−12 | 0.830 | 2.65E−14 |
| ENPP3 | RPS6KA6 | 0.787 | 2.46E−10 | 0.610 | 1.60E−06 |
| BNIP3 | ENPP5 | 0.470 | 1.29E−03 | 0.495 | 1.90E−04 |
| TUBA1B | RAP1B | 0.716 | 4.74E−08 | 0.620 | 9.44E−07 |
| | DYNLL1 | 0.644 | 2.43E−06 | 0.593 | 3.56E−06 |
| | RPS27L | 0.646 | 2.20E−06 | 0.568 | 1.12E−05 |

REFERENCES

1 Ferlay J, Shin H R, Bray F, et al. Estimates of worldwide burden of cancer in 2008: GLOBOCAN 2008. Int J Cancer 2010; 127:2893-917.

2 O'Connell J B, Maggard M A, Ko C Y. Colon cancer survival rates with the new American Joint Committee on Cancer sixth edition staging. J Natl Cancer Inst 2004; 96:1420-5.

3 NIH consensus conference. Adjuvant therapy for patients with colon and rectal cancer. JAMA 1990; 264:1444-50.

4 Figueredo A, Coombes M E, Mukherjee S. Adjuvant therapy for completely resected stage II colon cancer. Cochrane Database Syst Rev 2008; CD005390.

5 Benson A B, III, Schrag D, Somerfield M R, et al. American Society of Clinical Oncology recommendations on adjuvant chemotherapy for stage II colon cancer. J Clin Oncol 2004; 22:3408-19.

6 Gray R, Barnwell J, McConkey C, et al. Adjuvant chemotherapy versus observation in patients with colorectal cancer: a randomised study. Lancet 2007; 370:2020-9.

7 Farina-Sarasqueta A, van L G, Moerland E, et al. The BRAF V600E mutation is an independent prognostic factor for survival in stage II and stage III colon cancer patients. Ann Oncol 2010; 21:2396-402.

8 Roth A D, Tejpar S, Delorenzi M, et al. Prognostic role of KRAS and BRAF in stage II and III resected colon cancer: results of the translational study on the PETACC-3, EORTC 40993, SAKK 60-00 trial. J Clin Oncol 2010; 28:466-74.

9 Walther A, Houlston R, Tomlinson I. Association between chromosomal instability and prognosis in colorectal cancer: a meta-analysis. Gut 2008; 57:941-50.

10 Popat S, Hubner R, Houlston R S. Systematic review of microsatellite instability and colorectal cancer prognosis. J Clin Oncol 2005; 23:609-18.

11 Locker G Y, Hamilton S, Harris J, et al. ASCO 2006 update of recommendations for the use of tumor markers in gastrointestinal cancer. J Clin Oncol 2006; 24:5313-27.

12 Van S S, Allen W L, Turkington R C, et al. Implementing prognostic and predictive biomarkers in CRC clinical trials. Nat Rev Clin Oncol 2011; 8:222-32.

13 Jorissen R N, Gibbs P, Christie M, et al. Metastasis-Associated Gene Expression Changes Predict Poor Outcomes in Patients with Dukes Stage B and C Colorectal Cancer. Clin Cancer Res 2009; 15:7642-51.

14 Van Laar R K. An online gene expression assay for determining adjuvant therapy eligibility in patients with stage 2 or 3 colon cancer. Br J Cancer 2010; 103:1852-7.

15 Jiang Y, Casey G, Layery I C, et al. Development of a clinically feasible molecular assay to predict recurrence of stage II colon cancer. J Mol Diagn 2008; 10:346-54.

16 Bertucci F, Salas S, Eysteries S, et al. Gene expression profiling of colon cancer by DNA microarrays and correlation with histoclinical parameters. Oncogene 2004; 19; 23:1377-91.

17 Salazar R, Roepman P, Capella G, et al. Gene expression signature to improve prognosis prediction of stage II and III colorectal cancer. J Clin Oncol 2011; 29:17-24.

18 Smith J J, Deane N G, Wu F, et al. Experimentally derived metastasis gene expression profile predicts recurrence and death in patients with colon cancer. Gastroenterology 2010; 138:958-68.

19 Wang Y, Jatkoe T, Zhang Y, et al. Gene expression profiles and molecular markers to predict recurrence of Dukes' B colon cancer. J Clin Oncol 2004; 22:1564-71.

20 Berg M, Danielsen S A, Ahlquist T, et al. DNA sequence profiles of the colorectal cancer critical gene set KRAS-BRAF-PIK3CA-PTEN-TP53 related to age at disease onset. PLoS One 2010; 5:e13978.

21 Diep C B, Thorstensen L, Meling G I, et al. Genetic tumor markers with prognostic impact in Dukes' stages B and C colorectal cancer patients. J Clin Oncol 2003; 21:820-9.

22 Langfelder P, Horvath S. WGCNA: an R package for weighted correlation network analysis. BMC Bioinformatics 2008; 9:559.

23 Langfelder P, Horvath S. Package 'WGCNA'.

24 Smyth G K, Ritchie M, Thorne N, et al. limma: Linear Models for Microarray Data User's Guide.

25 Goeman J J. L1 penalized estimation in the Cox proportional hazards model. Biom J 2010; 52:70-84.

26 Goeamn J. Package 'penalized'.

27 Huang daW, Sherman B T, Lempicki R A. Systematic and integrative analysis of large gene lists using DAVID bioinformatics resources. Nat Protoc 2009; 4:44-57.

28 Quackenbush J. Microarray analysis and tumor classification. N Engl J Med 2006; 354:2463-72.

29 Tibshirani R. The lasso method for variable selection in the Cox model. Stat Med 1997; 16:385-95.

30 Tibshirani R. Regression shrinkage and seleciton via the LASSO. Journal of the Royal Statistical Society Series 1996; 58:267-88.

31 Agendia Inc. ColoPrint.

32 Genomic Health Inc. Oncotype DX colon cancer assay.

33 O'Connell M J, Layery I, Yothers G, et al. Relationship between tumor gene expression and recurrence in four independent studies of patients with stage II/III colon cancer treated with surgery alone or surgery plus adjuvant fluorouracil plus leucovorin. J Clin Oncol 2010; 28:3937-44.

34 PARSC study (NCT00903565): A Prospective Study for the Assessment of Recurrence Risk in Stage II Colon Cancer Patients Using ColoPrint (PARSC).

35 Clark-Langone K M, Wu J Y, Sangli C, et al. Biomarker discovery for colon cancer using a 761 gene RT-PCR assay. BMC Genomics 2007; 8:279.

36 Webber E M, Lin J S, Evelyn P W. Oncotype DX tumor gene expression profiling in stage II colon cancer. Application: prognostic, risk prediction. PLoS Curr 2010; 2.

37 Hanahan D, Weinberg R A. Hallmarks of cancer: the next generation. Cell 2011; 144:646-74.

38 Agesen T H, Berg M, Clancy T, et al. CLC and IFNAR1 are differentially expressed and a global immunity score is distinct between early- and late-onset colorectal cancer. Genes Immun 2011.

39 Kim J T, Song E Y, Chung K S, et al. Up-regulation and clinical significance of serine protease kallikrein 6 in colon cancer. Cancer 2011; 117:2608-19.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical sciences are intended to be within the scope of the following claims.

The invention claimed is:

1. A method for treating a human subject that has stage II colorectal cancer, comprising:
   a) extracting and reverse transcribing mRNA from a tumor sample from a human subject that has stage II colorectal cancer to provide complementary DNA;
   b) detecting the expression level of, SESN1, AZGP1, KLK6, EPHA7, and SEMA3A, mRNA transcripts, wherein said detection comprises contacting said complementary DNA with primers specific for complementary DNAs corresponding to, SESN1, AZGP1, KLK6, EPHA7, and SEMA3A, mRNA transcripts, amplifying said complementary DNAs; and quantifying the expression levels of said mRNA transcripts;
   c) determining that said human subject has altered expression of, SESN1, AZGP1, KLK6, EPHA7, and SEMA3A, mRNA transcripts,
   administering adjuvant chemotherapy to said human subject determined to have altered levels of expression of, SESN1, AZGP1, KLK6, EPHA7, and SEMA3A, mRNA transcripts, as compared to reference levels of expression, wherein said reference level is selected from the group consisting of the level in stage I colorectal cancer, the level in non-cancerous colorectal tissue, and the level in pre-cancerous colorectal tissue.

2. The method of claim 1, wherein said reference level is determined from multiple samples.

3. The method of claim 1, further comprising detecting the expression level of PIGR mRNA transcripts in addition to said SESN1, AZGP1, KLK6, EPHA7, and SEMA3A, mRNA transcripts, wherein said detection comprises contacting said complementary DNA with primers specific for complementary DNAs corresponding to said PIGR mRNA transcripts, amplifying said complementary DNAs; and quantifying the expression levels of said PIGR mRNA transcripts.

4. The method of claim 1, further comprising detecting the expression level of CXCL13 mRNA transcripts in addition to said SESN1, AZGP1, KLK6, EPHA7, and SEMA3A, mRNA transcripts, wherein said detection comprises contacting said complementary DNA with primers specific for complementary DNAs corresponding to said CXCL13 mRNA transcripts, amplifying said complementary DNAs; and quantifying the expression levels of said CXCL13 mRNA transcripts.

5. The method of claim 1, further comprising detecting the expression level of MMP3 mRNA transcripts in addition to said SESN1, AZGP1, KLK6, EPHA7, and SEMA3A, mRNA transcripts, wherein said detection comprises contacting said complementary DNA with primers specific for complementary DNAs corresponding to said MMP3 mRNA transcripts, amplifying said complementary DNAs; and quantifying the expression levels of said MMP3 mRNA transcripts.

6. The method of claim 1, further comprising detecting the expression level of TUBA1B mRNA transcripts in addition to said SESN1, AZGP1, KLK6, EPHA7, and SEMA3A, mRNA transcripts, wherein said detection comprises contacting said complementary DNA with primers specific for complementary DNAs corresponding to said TUBA1B mRNA transcripts, amplifying said complementary DNAs; and quantifying the expression levels of said TUBA1B mRNA transcripts.

7. The method of claim 1, further comprising detecting the expression level of DSC3 mRNA transcripts in addition to said SESN1, AZGP1, KLK6, EPHA7, and SEMA3A, mRNA transcripts, wherein said detection comprises contacting said complementary DNA with primers specific for complementary DNAs corresponding to said DSC3 mRNA transcripts, amplifying said complementary DNAs; and quantifying the expression levels of said DSC3 mRNA transcripts.

8. The method of claim 1, further comprising detecting the expression level of CXCL10 mRNA transcripts in addition to said SESN1, AZGP1, KLK6, EPHA7, and SEMA3A, mRNA transcripts, wherein said detection comprises contacting said complementary DNA with primers specific for complementary DNAs corresponding to said CXCL10 mRNA transcripts, amplifying said complementary DNAs; and quantifying the expression levels of said CXCL10 mRNA transcripts.

9. The method of claim 1, further comprising detecting the expression level of ENPP3 mRNA transcripts in addition to said SESN1, AZGP1, KLK6, EPHA7, and SEMA3A, mRNA transcripts, wherein said detection comprises contacting said complementary DNA with primers specific for complementary DNAs corresponding to said ENPP3 mRNA transcripts, amplifying said complementary DNAs; and quantifying the expression levels of said ENPP3 mRNA transcripts.

10. The method of claim 1, further comprising detecting the expression level of BNIP3 mRNA transcripts in addition to said SESN1, AZGP1, KLK6, EPHA7, and SEMA3A, mRNA transcripts, wherein said detection comprises contacting said complementary DNA with primers specific for complementary DNAs corresponding to said BNIP3mRNA transcripts, amplifying said complementary DNAs; and quantifying the expression levels of said BNIP3 mRNA transcripts.

\* \* \* \* \*